US010870616B2

(12) United States Patent
Scanlan et al.

(10) Patent No.: US 10,870,616 B2
(45) Date of Patent: *Dec. 22, 2020

(54) DERIVATIVES OF SOBETIROME

(71) Applicant: OREGON HEALTH & SCIENCE UNIVERSITY, Portland, OR (US)

(72) Inventors: Thomas Scanlan, Portland, OR (US); Jordan Devereaux, Portland, OR (US); Andrew Placzek, Portland, OR (US); Tapasree Banerji, Portland, OR (US); Skylar Ferrara, Portland, OR (US); James Matthew Meinig, Portland, OR (US); Tania Banerji, Portland, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/707,604

(22) Filed: Dec. 9, 2019

(65) Prior Publication Data

US 2020/0325092 A1    Oct. 15, 2020

Related U.S. Application Data

(63) Continuation of application No. 16/301,711, filed as application No. PCT/US2017/033388 on May 18, 2017, now Pat. No. 10,544,075.

(60) Provisional application No. 62/338,178, filed on May 18, 2016.

(51) Int. Cl.
| | |
|---|---|
| *C07C 43/315* | (2006.01) |
| *C07C 235/20* | (2006.01) |
| *C07C 59/115* | (2006.01) |
| *C07C 39/07* | (2006.01) |
| *C07C 65/34* | (2006.01) |
| *C07F 7/08* | (2006.01) |
| *A61P 25/28* | (2006.01) |

(52) U.S. Cl.
CPC ............ *C07C 43/315* (2013.01); *A61P 25/28* (2018.01); *C07C 39/07* (2013.01); *C07C 59/115* (2013.01); *C07C 65/34* (2013.01); *C07C 235/20* (2013.01); *C07F 7/0803* (2013.01); *C07B 2200/07* (2013.01)

(58) Field of Classification Search
CPC .................................................. C07C 43/315
See application file for complete search history.

(56) References Cited

U.S. PATENT DOCUMENTS

| 4,652,441 A | 3/1987 | Okada et al. |
|---|---|---|
| 4,675,189 A | 6/1987 | Kent et al. |
| 4,677,191 A | 6/1987 | Tanaka et al. |
| 4,728,721 A | 3/1988 | Yamamoto et al. |
| 4,917,893 A | 4/1990 | Okada et al. |
| 5,883,294 A | 3/1999 | Scanlan et al. |
| 6,107,517 A | 8/2000 | Scanlan et al. |
| 9,701,650 B2 | 7/2017 | Scanlan et al. |
| 10,130,643 B2 | 11/2018 | Cable et al. |
| 10,392,356 B2 | 8/2019 | Scanlan et al. |
| 2007/0021407 A1 | 1/2007 | Boyle et al. |
| 2016/0081955 A1 | 3/2016 | Scanlan et al. |

FOREIGN PATENT DOCUMENTS

| WO | 2017015360 | 1/2017 |
|---|---|---|
| WO | 2017201320 | 11/2017 |
| WO | 2018208707 A1 | 11/2018 |

OTHER PUBLICATIONS

U.S. Appl. No. 16/301,711, Notice of Allowability, dated Nov. 8, 2019, 2 pages.
U.S. Appl. No. 16/301,711, Notice of Allowance, dated Sep. 11, 2019, 9 pages.
Balkwill et al., "Smoldering and polarized inflammation in the initiation and promotion of malignant disease", Cancer Cell, vol. 7, 2005, pp. 211-217.
Baxi et al., "A selective thyroid hormone β receptor agonist enhances human", Glia 62(9), 2014, pp. 1513-1529.
Berge et al., "Pharmaceutical Salts", Journal of Pharmaceutical Sciences, vol. 66, No. 1, Jan. 1977, 19 pages.
Boger et al., "Fatty acid amide hydrolase substrate specificity", Bioorganic & medicinal chemistry letters 10.23, 2000, pp. 2613-2616.
Chiellini et al., "A high-affinity subtype-selective agonist ligand for the thyroid hormone receptor", Chemistry & Biology, vol. 5, No. 6, 1998, pp. 299-306.
Cravatt et al., "Supersensitivity to anandamide and enhanced endogenous cannabinoid signaling in mice lacking fatty acid amide hydrolase", Proceedings of the National Academy of Sciences of the United States of America vol. 98,16, 2001, pp. 9371-9376.
Ferrara et al., "Ester-to-amide Rearrangement of Ethanolamine-derived Prodrugs of Sobetirome With Increased Blood-brain Barrier Penetration", Bioorganic & Medicinal Chemistry; vol. 25, Issue 10, 2017, pp. 2743-2753.
Gold et al., "Understanding pathogenesis and therapy of multiple sclerosis via animal models: 70 years of merits and culprits in experimental autoimmune encephalomyelitis research", Brain 129, Aug. 2006, pp. 1953-1971.
Grover et al., "Effects of the Thyroid Hormone Receptor Agonist GC-1 on Metabolic Rate and Cholesterol in Rats and Primates: Selective Actions Relative to 3,5,3'-Triiodo-L-Thyronine", Endocrinology 145(4), Apr. 1, 2004, pp. 1656-1661.

(Continued)

*Primary Examiner* — Shawquia Jackson

(74) *Attorney, Agent, or Firm* — Kilpatrick Townsend & Stockton LLP

(57) ABSTRACT

Disclosed are halo substituted derivative compounds of sobetirome with improved pharmacological characteristics relative to sobetirome, pharmaceutical compositions that include those compounds and methods of treating diseases such as neurodegenerative disorders using those pharmaceutical compositions.

25 Claims, 7 Drawing Sheets

(56) References Cited

OTHER PUBLICATIONS

Hartley et al., "A Thyroid Hormone-Based Strategy for Correcting the Biochemical Abnormality in X-Linked Adrenoleukodystrophy", Endocrinology, vol. 158, Issue 5, May 2017, pp. 1328-1338.
Miyabara, et al. "Thyroid Hormone Receptor-β-Selective Agonist GC-24 Spares Skeletal Muscle Type I to II Fiber Shift," Cell and Tissue Research, vol. 321, Issue 2, Aug. 2005, pp. 233-241.
Ocasio et al., "Characterization of thyroid hormone receptor alpha (TRalpha)-specific analogs with varying inner- and outer-ring substituents", Bioorg Med Chem.16(2), 2007, pp. 762-770.
Ocasio et al., "Design and characterization of a thyroid hormone receptor a (TRα)-specific agonist", ACS Chemical Biology 1.9, 2006, pp. 585-593.
O'Shea et al., "Characterization of skeletal phenotypes of TRalpha1 and TRbeta mutant mice: implications for tissue thyroid status and T3 target gene expression", Nuclear receptor signaling vol. 4, 2006, e011.
PCT/US2017/033388, "International Preliminary Report on Patentability", dated Nov. 29, 2018, 10 pages.
PCT/US2017/033388, "International Search Report and Written Opinion", dated Aug. 16, 2017, 11 pages.
PCT/US2019/017881, "International Search Report and Written Opinion", dated May 13, 2019, 9 pages.
Placzek et al., "New synthetic routes to thyroid hormone analogs: d6-sobetirome, 3H-sobetirome, and the antagonist NH-3", Tetrahedron 71(35), 2015, pp. 5946-5951.
Tancevski et al., "The resurgence of thyromimetics as lipid-modifying agents", Current Opinion in Investigational Drugs, vol. 10, No. 9, Sep. 2009, pp. 912-918.
Trost et al., "The Thyroid Hormone Receptor-β-Selective Agonist GC-1 Differentially Affects Plasma Lipids and Cardiac Activity", Endocrinology, vol. 141, Issue 9, Sep. 1, 2000, pp. 3057-3064.
Yen et al., "Physiological and Molecular Basis of Thyroid Hormone Action", Physiol. Rev. 81(3), 2001, pp. 1097-1142.
Devereaux et al., "Increasing Thyromimetic Potency Through Halogen Substitution", *ChemMedChem*. 11(21), Nov. 7, 2016, 2459-2465.
PCT/US2019/017881, International Preliminary Report on Patentability, dated Jul. 24, 2020, 5 pages.
RU2018142863, Office Action and Search Report, dated Jul. 13, 2020, 18 pages.

DERIVATIVES OF SOBETIROME

CROSS-REFERENCES TO RELATED APPLICATIONS

The present application is a continuation of a U.S. application Ser. No. 16/301,711 filed on Nov. 14, 2018, which is the National stage of International Application No. PCT/US2017/03338 filed on May 18, 2017 and which claims priority to U.S. Provisional Pat. Appl. No. 62/338,178, filed on May 18, 2016, which applications are incorporated herein by reference in their entirety.

STATEMENT AS TO RIGHTS TO INVENTIONS MADE UNDER FEDERALLY SPONSORED RESEARCH AND DEVELOPMENT

This invention was made with government support under grant number DK-52798 awarded by the National Institutes of Health. The government has certain rights in the invention.

BACKGROUND OF THE INVENTION

Thyroid hormone (TH) is a key signal for oligodendrocyte differentiation and myelin formation during development and also stimulates remyelination in adult models of multiple sclerosis (MS) (Calzà. L et al. *Brain Res Revs* 48, 339-346 (2005); incorporated by reference herein.) However, TH is not an acceptable long-term therapy due to there being virtually no therapeutic window in which remyelination can be achieved while avoiding the cardiotoxicity and bone demineralization associated with chronic hyperthyroidism. Some thyroid hormone analogs can activate thyroid hormone-responsive genes while avoiding the associated downsides of TH by exploiting molecular and physiological features of thyroid hormone receptors (Maim J et al. *Mini Rev Med Chem* 7, 79-86 (2007); incorporated by reference herein). These receptors are expressed in two major forms with heterogenous tissue distributions and overlapping but distinct sets of target genes (Yen P M, *Physiol Rev* 81, 1097-1142 (2001); incorporated by reference herein). TRα is enriched in the heart, brain, and bone while TRβ is enriched in the liver (O'Shea P J et al. *Nucl Recept Signal* 4, e011 (2006); incorporated by reference herein). Developing selective thyromimetics has been challenging due to the high sequence homology of thyroid hormone receptor subtypes—only one amino acid residue on the internal surface of the ligand binding domain cavity varies between the al and (31 forms. GC-1 was one of the first potent analogs that demonstrated significant TRβ-selectivity in vitro (Chiellini G et al. *Chem Biol* 5, 299-306 (1998) and Yoshihara H A I et al. *J Med Chem* 46, 3152-3161 (2003); both of which are incorporated by reference herein) and in vivo (Trost S U et al. *Endocrinology* 141, 3057-3064 (2000); Grover G J et al. *Endocrinology* 145, 1656-1661 (2004); and Baxter J D et al. *Trends Endocrinol Metab* 15, 154-157 (2004); all of which are incorporated by reference herein).

BRIEF SUMMARY OF THE INVENTION

Disclosed herein are compounds according to Formula I:

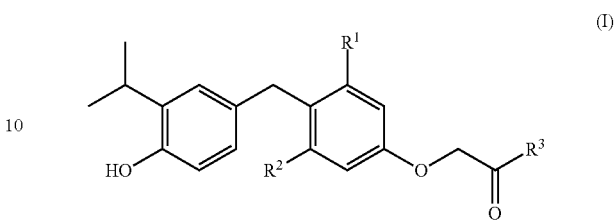

(I)

or any pharmaceutically acceptable salt thereof, wherein:
$R^1$ and $R^2$ are independently selected from the group consisting of fluoro, chloro, bromo, and iodo, and
$R^3$ is independently selected from the group consisting of —OH and —$NR^{3a}R^{3b}$,
$R^{3a}$ is independently selected from the group consisting of hydrogen and $C_{1-6}$ alkyl, and
$R^{3b}$ is $C_{1-6}$ alkyl.

Also disclosed are pharmaceutical compositions comprising an effective amount of the disclosed compounds or a pharmaceutically acceptable salt thereof and one or more pharmaceutically acceptable carriers. In some examples, the pharmaceutical composition is for use in treating a neurodegenerative disorder including neurodegenerative disorders classified as a demyelinating disease such as X-linked adrenoleukodystrophy or multiple sclerosis.

Also disclosed are methods of treating a neurodegenerative disorder in a subject, such methods involve administering the disclosed pharmaceutical compositions to the subject, thereby treating the neurodegenerative disorder. In some aspects, the neurodegenerative disorder can be classified as a demyelinating disease such as X-linked adrenoleukodystrophy or multiple sclerosis.

DETAILED DESCRIPTION OF THE INVENTION

I. Definitions

Figure 1A:
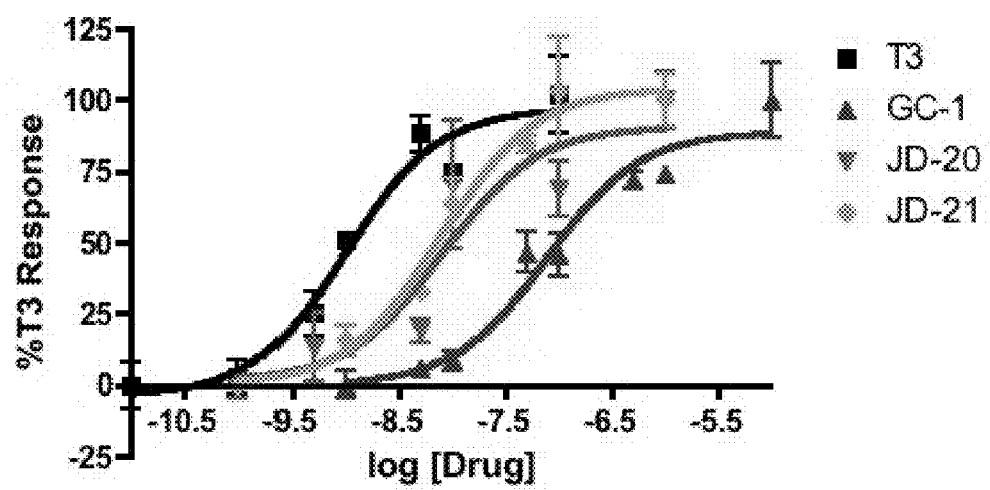
FIG. 1A is a plot of the data from a TRE-driven dual luciferase transactivation assays with calculated sigmoidal dose-response curves against hTRα1 in transiently transfected HEK293 cells. Plots show means of triplicates with error bars normalized to T3 response.

Unless specifically defined otherwise, the technical terms, as used herein, have their normal meaning as understood in the art. The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Variables such as R, including all subvariables thereof (such as $R^1$, $R^2$, etc.) used throughout the disclosure are the same variables as previously defined unless stated to the contrary.

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc.

As used herein, the terms "acute disseminated encephalomyelitis" and "ADEM" refer to an immune-mediated demyelinating disease of the central nervous system. ADEM usually occurs following a viral infection, but may also appear following vaccination or following bacterial or parasitic infection. In some cases, ADEM develops spontaneously. The disease involves autoimmune demyelination, similar to multiple sclerosis, and is therefore considered a multiple sclerosis borderline disease. ADEM produces multiple inflammatory lesions in the brain and spinal cord, particularly in the white matter. The lesions are typically found in the subcortical and central white matter and cortical gray-white junction of both cerebral hemispheres, cerebellum, brainstem, and spinal cord, but periventricular white matter and gray matter of the cortex, thalami and basal ganglia may also be involved. When a patient suffers more than one demyelinating episode, the disease is referred to as recurrent disseminated encephalomyelitis or multiphasic disseminated encephalomyelitis.

As used herein, the terms "acute hemorrhagic leukoencephalitis," "AHL," and "AHLE" refer to a hyperacute and frequently fatal form of ADEM. This disease is also known as acute necrotizing encephalopathy (ANE), acute hemorrhagic encephalomyelitis (AHEM), acute necrotizing hemorrhagic leukoencephalitis (ANHLE), Weston-Hurst syndrome, or Hurst's disease.

As used herein, the term "administration" refers to providing a compound, a prodrug of a compound, or a pharmaceutical composition comprising a compound or prodrug as described herein. The compound or composition can be administered by another person to the subject or it can be self-administered by the subject.

As used herein, the term "adult Refsum disease" refers to an autosomal recessive neurological disease that is associated with the over-accumulation of phytanic acid in cells and tissues. Adult Refsum disease is divided into the adult Refsum disease 1 and adult Refsum disease 2 subtypes. Individuals with Refsum disease present with neurologic damage, cerebellar degeneration, and peripheral neuropathy. Onset is most commonly in childhood/adolescence with a progressive course, although periods of stagnation or remission occur. Symptoms also include ataxia, scaly skin (ichthyosis), difficulty hearing, and eye problems including cataracts and night blindness.

As used herein, the term "Alexander disease" refers to a very rare, congenital demyelinating disease. The disease primarily affects infants and children, causing developmental delay and changes in physical characteristics. Alexander disease is a type of leukodystrophy.

As used herein, the term "Alzheimer's disease" refers to the most common form of dementia. Symptoms of Alzheimer's disease include memory loss, confusion, irritability, aggression, mood swings and trouble with language. This disease is characterized by the loss of neurons and synapses in the cerebral cortex and certain subcortical regions. The loss results in gross atrophy of the affected regions, including degeneration in the temporal lobe, and parts of the frontal cortex and cingulate gyrus. Amyloid plaques and neurofibrillary tangles are visible by microscopy in brains of those afflicted with this disease. The cause of Alzheimer's disease is unknown; however, several hypotheses exist, including that the disease is caused by age-related myelin breakdown in the brain.

As used herein, the term "Balo concentric sclerosis" refers to a demyelinating disease similar to standard multiple sclerosis, but with the particularity that the demyelinated tissues form concentric layers. Patients with this disease can survive and/or have spontaneous remission. Typically, the clinical course is primary progressive, but a relapsing-remitting course has been reported.

As used herein, the term "Canavan disease" refers to an autosomal recessive degenerative disorder that causes progressive damage to nerve cells in the brain. Canavan disease is a leukodystrophy and is one of the most common degenerative cerebral diseases of infancy. This disease is also called Canavan-Van Bogaert-Bertrand disease, aspartoacylase deficiency and aminoacylase 2 deficiency.

As used herein, the terms "Central pontine myelinolysis" and "CPM" refer to a neurologic disease caused by severe damage of the myelin sheath of nerve cells in the brainstem, more precisely in the area termed the pons. The most common cause is the rapid correction of low blood sodium levels (hyponatremia). Frequently observed symptoms in this disorder are sudden para or quadraparesis, dysphagia, dysarthria, diplopia and loss of consciousness. The patient may experience locked-in syndrome where cognitive function is intact, but all muscles are paralyzed with the exception of eye blinking.

As used herein, the term "cerebral palsy" refers to a group of permanent, non-progressive movement disorders that cause physical disability. Cerebral palsy is caused by damage to the motor control centers of the developing brain and can occur during pregnancy, during childbirth, or after birth up to about age three. Patients with cerebral palsy exhibit damage to myelin sheaths.

As used herein, the term "cerebrotendineous xanthomatosis" refers to an inherited disorder associated with the deposition of a form of cholesterol (cholestanol) in the brain and other tissues and with elevated levels of cholesterol in plasma but with normal total cholesterol level. It is characterized by progressive cerebellar ataxia beginning after puberty and by juvenile cataracts, juvenile or infantile onset chronic diarrhea, childhood neurological deficit, and tendineous or tuberous xanthomas. This disorder is an autosomal recessive form of xanthomatosis. It falls within a group of genetic disorders called the leukodystrophies.

As used herein, the terms "chronic inflammatory demyelinating polyneuropathy" and "CIDP" refer to an acquired immune-mediated inflammatory disorder of the peripheral nervous system. The disorder is sometimes called chronic relapsing polyneuropathy (CRP) or chronic inflammatory demyelinating polyradiculoneuropathy (because it involves the nerve roots). CIDP is closely related to Guillain-Barré syndrome and it is considered the chronic counterpart of that acute disease. Its symptoms are also similar to progressive inflammatory neuropathy. An asymmetrical variant of CIDP is known as Lewis-Sumner syndrome. The pathologic hallmark of the disease is loss of the myelin sheath.

As used herein, the term "demyelinating disease" refers to any disease of the nervous system in which myelin is damaged or lost, or in which the growth or development of the myelin sheath is impaired. Demyelination inhibits the conduction of signals in the affected nerves, causing impairment in sensation, movement, cognition, or other functions for which nerves are involved. Demyelinating diseases have a number of different causes and can be hereditary or acquired. In some cases, a demyelinating disease is caused by an infectious agent, an autoimmune response, a toxic agent or traumatic injury. In other cases, the cause of the demyelinating disease is unknown ("idiopathic") or develops from a combination of factors.

As used herein, the term "derivative" refers to a compound or portion of a compound that is derived from or is theoretically derivable from a parent compound.

As used herein, the term "Devic's syndrome" refers to an autoimmune, inflammatory disorder in which a person's immune system attacks the optic nerves and spinal cord, which results in inflammation of the optic nerve (optic neuritis) and the spinal cord (myelitis). Spinal cord lesions lead to varying degrees of weakness or paralysis in the legs or arms, loss of sensation, and/or bladder and bowel dysfunction. Although inflammation may also affect the brain, the lesions are different from those observed in MS. Devic's syndrome is similar to MS in that the body's immune system attacks the myelin surrounding nerve cells. Unlike standard MS, the attacks are not believed to be mediated by the immune system's T cells but rather by antibodies called NMO-IgG. These antibodies target a protein called aquaporin 4 in the cell membranes of astrocytes which acts as a channel for the transport of water across the cell membrane. Devic's syndrome is also known as Devic's syndrome or neuromyelitis optica (NMO).

As used herein, the term "diffuse myelinoclastic sclerosis" refers to an uncommon neurodegenerative disease that presents clinically as pseudotumoral demyelinating lesions. It usually begins in childhood, affecting children between 5 and 14 years old; however, cases in adults are possible. This disease is considered one of the borderline forms of MS and is sometimes referred to as Schilder's disease.

As used herein, the term "effective amount" refers to a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

As used herein, the term "encephalomyelitis" refers to inflammation of the brain and spinal cord.

As used herein, the terms "experimental autoimmune encephalomyelitis" and "EAE" refer to an animal model of MS (for example, see Gold et al. *Brain* 129, 1953-1971 (2006). EAE animals exhibit characteristic plaques of tissue injury disseminated throughout the central nervous system. Plaques show infiltration of nervous tissue by lymphocytes, plasma cells, and macrophages, which cause destruction of the myelin sheaths that surround nerve cell axons in the brain and spinal cord. In some cases, EAE is induced by immunization of susceptible animals, such as mice, rats, guinea pigs, or non-human primates, with either myelin or various components of myelin. For example, EAE can be induced by immunization with components of the myelin sheath, such as myelin basic protein, proteolipid protein, or myelin oligodendrocyte glycoprotein (MOG). EAE is a useful and widely accepted model for studying mechanisms of autoimmune CNS tissue injury and for testing potential therapies for MS. EAE also includes "passive EAE" which is induced in the same manner in donor animals, but involves the transfer of activated T-cells harvested from the donor animal's lymph nodes to naïve recipient animals.

As used herein, the term "Guillain-Barré syndrome" refers to an acute polyneuropathy, a disorder affecting the peripheral nervous system. Ascending paralysis, weakness beginning in the feet and hands and migrating towards the trunk, is the most typical symptom, and some subtypes cause change in sensation or pain, as well as dysfunction of the autonomic nervous system. It can cause life-threatening complications, in particular if the respiratory muscles are affected or if the autonomic nervous system is involved. This disease is usually triggered by an infection. Acute inflammatory demyelinating polyneuropathy (AIDP) is the most common subtype of this disease. Other subtypes of Guillain-Barré syndrome include Miller Fischer syndrome, acute motor axonal neuropathy (Chinese paralytic syndrome), acute motor sensory axonal neuropathy, acute panautonomic neuropathy, and Bickerstaff's brainstem encephalitis.

As used herein, the term "hemorrhage" refers to bleeding or escape of blood from a vessel.

As used herein, the term "hypoxia" refers to the lack of oxygen supply to the tissues of the body below the normal level.

As used herein, the terms "idiopathic inflammatory demyelinating disease" and "IIDD" refer to a broad spectrum of central nervous system disorders that can usually be differentiated on the basis of clinical, imaging, laboratory and pathological findings. Idiopathic inflammatory demyelinating diseases are sometimes known as borderline forms of multiple sclerosis. IIDD generally refers to a collection of multiple sclerosis variant diseases, including but not limited to, optic-spinal MS, Devic's disease, ADEM, acute hemorrhagic leukoencephalitis, Balo concentric sclerosis, Schilder disease, Marburg multiple sclerosis, tumefactive multiple sclerosis and solitary sclerosis.

As used herein, the term "infantile Refsum disease" refers to a peroxisome biogenesis disorder associated with deficiencies in the catabolism of very long chain fatty acids and branched chain fatty acids (such as phytanic acid) and plasmalogen biosynthesis. Infantile Refsum disease is a rare, autosomal recessive congenital disorder, and one of three peroxisome biogenesis disorders that belong to the Zellweger spectrum of peroxisome biogenesis disorders.

As used herein, the term "injury" refers to any type of physical damage to cells, tissues, or the body. In some cases, nervous system (e.g., CNS or PNS) injury results in demyelination and/or a demyelinating disease.

As used herein, the term "ischemia" refers to a vascular phenomenon in which a decrease in the blood supply to a bodily organ, tissue, or part is caused, for instance, by constriction or obstruction of one or more blood vessels. Ischemia sometimes results from vasoconstriction, thrombosis or embolism. Ischemia can lead to direct ischemic injury, tissue damage due to cell death caused by reduced oxygen supply. In some cases, ischemia can lead to demyelination.

As used herein, the term "Krabbe disease" refers to a rare, often fatal degenerative disorder that affects the myelin sheath of the nervous system. It is a form of sphingolipidosis, as it involves dysfunctional metabolism of sphingolipids. This condition is inherited in an autosomal recessive pattern. Krabbe disease is also known as globoid cell leukodystrophy or galactosylceramide lipidosis.

As used herein, the term "Leber hereditary optic neuropathy" refers to a mitochondrially inherited (transmitted from mother to offspring) degeneration of retinal ganglion cells (RGCs) and their axons that leads to an acute or subacute loss of central vision; this affects predominantly young adult males.

As used herein, the term "leukodystrophy" refers to a group of diseases that affects the growth or development of the myelin sheath.

As used herein, the term "leukoencephalopathy" refers to any of a group of diseases affecting the white substance of the brain; can refer specifically to several diseases including, for example, "leukoencephalopathy with vanishing white matter" and "toxic leukoencephalopathy." Leukoencephalopathies are leukodystrophy-like diseases.

As used herein, the term "Marburg multiple sclerosis" refers to a condition in which the central nervous system has multiple demyelinating lesions with atypical characteristics for those of standard multiple sclerosis. This disease is a borderline form of multiple sclerosis and is also known as tumefactive multiple sclerosis or fulminant multiple sclerosis. It is called tumefactive because the lesions are "tumor-like" and they mimic tumors clinically, radiologically and sometimes pathologically.

As used herein, the term "Marchiafava-Bignami disease" refers to a progressive neurological disease characterized by corpus callosum demyelination and necrosis and subsequent atrophy. It is classically associated with chronic alcoholics.

As used herein, the terms "metachromatic leukodystrophy" and "MLD" refer to a lysosomal storage disease that is commonly listed in the family of leukodystrophies, as well as in the sphingolipidoses as it affects the metabolism of sphingolipids. MLD is directly caused by a deficiency of the enzyme arylsulfatase A.

As used herein, the terms "multifocal motor neuropathy" and "MMN" refer to a progressively worsening condition where muscles in the extremities gradually weaken. This disorder, a motor neuropathy syndrome, is sometimes mistaken for amyotrophic lateral sclerosis (ALS) because of the similarity in the clinical picture, especially if muscle fasciculations are present. MMN is usually asymmetric and is thought to be autoimmune.

As used herein, the terms "multiple sclerosis" and "MS" refer to a slowly progressive CNS disease characterized by disseminated patches of demyelination in the brain and spinal cord, resulting in multiple and varied neurological symptoms and signs, usually with remissions and exacerbation. The cause of MS is unknown but an immunological abnormality is suspected. An increased family incidence suggests genetic susceptibility, and women are somewhat more often affected than men. The symptoms of MS include weakness, lack of coordination, paresthesias, speech disturbances, and visual disturbances, most commonly double vision. More specific signs and symptoms depend on the location of the lesions and the severity and destructiveness of the inflammatory and sclerotic processes. Relapsing-remitting multiple sclerosis (RRMS) is a clinical course of MS that is characterized by clearly defined, acute attacks with full or partial recovery and no disease progression between attacks. Secondary-progressive multiple sclerosis (SPMS) is a clinical course of MS that initially is relapsing-remitting, and then becomes progressive at a variable rate, possibly with an occasional relapse and minor remission. Primary-progressive multiple sclerosis (PPMS) presents initially in the progressive form. A clinically isolated syndrome is the first neurologic episode, which is caused by inflammation/demyelination at one or more sites in the CNS. Progressive-relapsing multiple sclerosis (PRMS) is a rare form of MS (~5%) characterized by a steadily worsening disease state from onset, with acute relapses but no remissions.

As used herein, the term "myelin" refers to a lipid substance forming a sheath (known as the myelin sheath) around the axons of certain nerve fibers. Myelin is an electrical insulator that serves to speed the conduction of nerve impulses in nerve fibers. "Myelination" (also "myelinization") refers to the development or formation of a myelin sheath around a nerve fiber. Similarly, "remyelination" (also, "remyelinization") refers to the repair or reformation of the myelin sheath, such as following injury, exposure to a toxic agent, or an inflammatory response, or during the course of a demyelinating disease.

As used herein, the term "neurodegenerative disease" refers to any type of disease that is characterized by the progressive deterioration of the nervous system.

As used herein, the term "neuropathy" refers to a functional disturbance or pathological change in the peripheral nervous system. Axonal neuropathy refers to a disorder disrupting the normal functioning of the axons.

As used herein, the term "paraproteinemic demyelinating polyneuropathy" refers to a type of peripheral neuropathy characterized by auto antibodies directed against myelin associated glycoproteins (MAG). Anti-MAG antibodies inhibit the production of myelin, thereby leading to neuropathy.

As used herein, the terms "Pelizaeus-Merzbacher disease" and "PMD" refer to a rare central nervous system disorder in which coordination, motor abilities, and intellectual function are delayed to variable extents. The disease is one in a group of genetic disorders collectively known as leukodystrophies.

As used herein, the terms "peroneal muscular atrophy" and "PMA" refer to a genetically and clinically heterogeneous group of inherited disorders of the peripheral nervous system characterized by progressive loss of muscle tissue and touch sensation across various parts of the body. This disease is also known as Charcot-Marie-Tooth disease (CMT), Charcot-Marie-Tooth neuropathy and hereditary motor and sensory neuropathy (HMSN).

As used herein, the term "pharmaceutical composition" refers to a composition containing one or more of the compounds described herein, or a pharmaceutically acceptable salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

As used herein, the term "pharmaceutically acceptable carrier" refers to any ingredient other than the disclosed compounds, or a pharmaceutically acceptable salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

As used herein, the term "pharmaceutically acceptable salt" refers to salts prepared by conventional methods. These include basic salts of inorganic and organic acids, such as, without limitation, hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, and mandelic acid. "Pharmaceutically acceptable salts" of the presently disclosed compounds also include those formed from cations such as, without limitation, sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reaction of the free acid with a suitable organic or inorganic base. Any chemical compound recited in this specification may alternatively be administered as a pharmaceutically acceptable salt thereof. Pharmaceutically acceptable salts are also inclusive of the free acid, base, and zwitterionic forms of the disclosed compounds. Descriptions of exemplary pharmaceutically acceptable salts can be found in Stahl and Wermuth, Eds., *Handbook of Pharmaceutical Salts; Properties, Selection and Use*, Wiley VCH (2008). When the compounds disclosed herein include an acidic group such as a carboxy group, then suitable pharmaceutically acceptable cation pairs for the carboxy group are well known to those skilled in the art and include, without limitation, alkaline, alkaline earth, ammonium, and quaternary ammonium cations. Such salts are known to those of skill in the art. Similarly when the compounds disclosed herein include a basic group such as an amino group, then suitable pharmaceutically acceptable anion pairs for the basic group are similarly well known and include halide, hydroxide, perhalate, halite, hypohalite, sulfate, sulfite, phosphate, phosphite, nitrate, nitrite, and others known to those of skill in the art. For additional examples of pharmacologically acceptable salts, see Berge et al. *J. Pharm. Sci.* 66, 1 (1977).

As used herein, the terms "progressive multifocal leukoencephalopathy" and "PML" refer to rare and usually fatal viral disease that is characterized by progressive damage or inflammation of the white matter of the brain in multiple locations. PML occurs almost exclusively in people with severe immune deficiency. The cause of PML is a type of polyomavirus called the JC virus. The virus is widespread, with 86% of the general population presenting antibodies, but it usually remains latent, causing disease only when the immune system has been severely weakened. PML is a demyelinating disease, in which the myelin sheath covering the axons of nerve cells is gradually destroyed, impairing the transmission of nerve impulses. The disease may occur in subjects (e.g., humans) with severe immune deficiency, such as transplant patients on immunosuppressive medications or those receiving certain kinds of medications. For example, PML has been associated with administration of rituximab (off-label use in the treatment of multiple sclerosis). It affects the white matter, which is mostly composed of axons from the outermost parts of the brain (cortex). Symptoms include weakness or paralysis, vision loss, impaired speech, and cognitive deterioration.

As used herein, the term "sobetirome" refers to a synthetic diarylmethane derivative that was investigated clinically as a potential therapeutic for hypercholesterolemia (see U.S.

Pat. No. 5,883,294, which is incorporated by reference herein). Other names for sobetirome found in the literature and regulatory filings include QRX-431 and GC-1. Sobetirome is also referred to herein as compound 1.

As used herein, the term "subject" refers to an animal (e.g., a mammal, such as a human). A subject to be treated according to the methods described herein may be one who has been diagnosed with a neurodegenerative disease involving demyelination, insufficient myelination, or underdevelopment of a myelin sheath, e.g., a subject diagnosed with multiple sclerosis or cerebral palsy, or one at risk of developing the condition. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

As used herein, the term "transverse myelitis" refers to a neurological disorder caused by an inflammatory process of the grey and white matter of the spinal cord, leading to axonal demyelination. Demyelination arises idiopathically following infections or vaccination, or due to multiple sclerosis. Symptoms include weakness and numbness of the limbs as well as motor, sensory, and sphincter deficits. Severe back pain may occur in some patients at the onset of the disease.

As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

As used herein, the terms "tropical spastic paraparesis" and "TSP" refer to an infection of the spinal cord by human T-lymphotropic virus resulting in paraparesis, weakness of the legs. TSP is also known as HTLV associated myelopathy or chronic progressive myelopathy. As the name suggests, this disease is most common in tropical regions, including the Caribbean and Africa.

As used herein, the term "Van der Knaap disease" refers to a form of hereditary CNS demyelinating disease. This disease is a type of leukodystrophy and is also known as megalencephalic leukoencephalopathy with subcortical cysts (MLC).

As used herein, the terms "X-linked adrenoleukodystrophy," "X-ALD," "ALD," and "X-linked ALD" refer to a rare, inherited metabolic disorder that leads to progressive brain damage, mental deterioration, failure of the adrenal glands, muscle spasms, blindness and eventually death. ALD is one disease in a group of inherited disorders called leukodystrophies. Adrenoleukodystrophy progressively damages myelin. X-linked ALD male patients may be divided into 7 phenotypes: childhood cerebral (progressive neurodegenerative decline leading to a vegetative state), adolescent (similar to childhood cerebral form but with a slower progression), adrenomyeloneuropathy (progressive neuropathy, paraparesis, may progress to cerebral involvement), adult cerebral (dementia, similar progression to childhood cerebral form), olivo-ponto-cerebellar (cerebral and brain stem involvement), Addison disease (adrenal insufficiency), asymptomatic (no clinical presentation, subclinical adrenal insufficiency, or AMN phenotype). X-linked ALD female patients may be divided into 5 phenotypes: asymptomatic (no neurologic or adrenal involvement), mild myelopathy, moderate to severe myelopathy (similar to male AMN phenotype), cerebral (progressive dementia and decline), and adrenal (primary adrenal insufficiency). X-linked ALD patients may progress from one phenotype to another over the course of their life. ALD is also known as Addison-Schilder disease or Siemerling-Creutzfeldt disease.

As used herein, the term "Zellweger syndrome" refers to a rare congenital disorder, characterized by the reduction or absence of functional peroxisomes in the cells of an individual. This disease is classified as a leukodystrophy and is one of three peroxisome biogenesis disorders that belong to the Zellweger spectrum of peroxisome biogenesis disorders.

II. Sobetirome Derivatives

In a first aspect, the invention provides a compound according to Formula I:

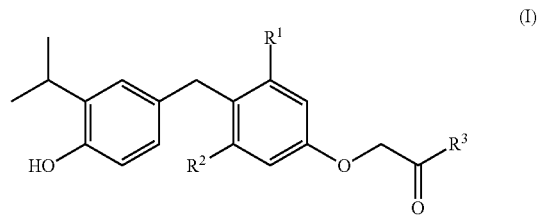

or any pharmaceutically acceptable salt thereof, wherein:
$R^1$ and $R^2$ are independently selected from the group consisting of fluoro, chloro, bromo, and iodo, and
$R^3$ is independently selected from the group consisting of —OH and —NR$^{3a}$R$^{3b}$,
$R^{3a}$ is independently selected from the group consisting of hydrogen and $C_{1-6}$ alkyl, and
$R^{3b}$ is $C_{1-6}$ alkyl.

In some embodiments, $R^1$ is fluoro and $R^2$ is selected from the group consisting of chloro, bromo, and iodo; or $R^1$ is chloro and $R^2$ is selected from the group consisting of fluoro, bromo, and iodo; or $R^1$ is bromo and $R^2$ is selected from the group consisting of fluoro, chloro, and iodo; or $R^1$ is iodo and $R^2$ is selected from the group consisting of fluoro, chloro, and bromo.

In some embodiments, $R^2$ is fluoro and $R^1$ is selected from the group consisting of chloro, bromo, and iodo; or $R^2$ is chloro and $R^1$ is selected from the group consisting of fluoro, bromo, and iodo; or $R^2$ is bromo and $R^1$ is selected from the group consisting of fluoro, chloro, and iodo; or $R^2$ is iodo and $R^1$ is selected from the group consisting of fluoro, chloro, and bromo.

In some embodiments, $R^3$ is —OH, $R^1$ is fluoro, and $R^2$ is selected from the group consisting of chloro, bromo, and iodo; or $R^3$ is —OH, $R^1$ is chloro, and $R^2$ is selected from the group consisting of fluoro, bromo, and iodo; or $R^3$ is —OH, $R^1$ is bromo, and $R^2$ is selected from the group consisting of fluoro, chloro, and iodo; or R³ is —OH, R¹ is iodo, and R² is selected from the group consisting of fluoro, chloro, and bromo.

In some embodiments, R³ is —OH, R² is fluoro, and R¹ is selected from the group consisting of chloro, bromo, and iodo; or R³ is —OH, R² is chloro, and R¹ is selected from the group consisting of fluoro, bromo, and iodo; or R³ is —OH, R² is bromo, and R¹ is selected from the group consisting of fluoro, chloro, and iodo; or R³ is —OH, R² is iodo, and R¹ is selected from the group consisting of fluoro, chloro, and bromo.

In some embodiments, R³ is —NHR$^{3b}$, R¹ is fluoro, and R² is selected from the group consisting of chloro, bromo, and iodo; or R³ is —NHR$^{3b}$, R¹ is chloro, and R² is selected from the group consisting of fluoro, bromo, and iodo; or R³ is —NHR$^{3b}$, R¹ is bromo, and R² is selected from the group consisting of fluoro, chloro, and iodo; or R³ is —NHR$^{3b}$, R¹ is iodo, and R² is selected from the group consisting of fluoro, chloro, and bromo. In some such embodiments, R$^{3b}$ is C$_{1-6}$ alkyl. R$^{3b}$ can be, for example, methyl, ethyl, n-propyl, isopropyl, n-butyl, isobutyl, sec-butyl, tert-butyl, n-pentyl, branched pentyl, n-hexyl, or branched hexyl. In some embodiments, R$^{3b}$ is methyl.

In some embodiments, R³ is —NHR$^{3b}$, R² is fluoro, and R¹ is selected from the group consisting of chloro, bromo, and iodo; or R³ is —NHR$^{3b}$, R² is chloro, and R¹ is selected from the group consisting of fluoro, bromo, and iodo; or R³ is —NHR$^{3b}$, R² is bromo, and R¹ is selected from the group consisting of fluoro, chloro, and iodo; or R³ is —NHR$^{3}$b, R² is iodo, and R¹ is selected from the group consisting of fluoro, chloro, and bromo. In some such embodiments, R$^{3b}$ is C$_{1-6}$ alkyl. R$^{3b}$ can be, for example, methyl, ethyl, n-propyl, isopropyl, n-butyl, isobutyl, sec-butyl, tert-butyl, n-pentyl, branched pentyl, n-hexyl, or branched hexyl. In some embodiments, R$^{3b}$ is methyl.

In some embodiments, R¹ and R² are independently selected from the group consisting of chloro and bromo.

In some embodiments, R¹ and R² are both bromo. In some embodiments, R¹ and R² are both bromo, and R³ is —OH.

In some embodiment, R¹ and R² are both bromo, R³ is —NHR$^{3b}$, and R$^{3b}$ is C$_{1-6}$ alkyl. R$^{3b}$ can be, for example, methyl, ethyl, n-propyl, isopropyl, n-butyl, isobutyl, sec-butyl, tert-butyl, n-pentyl, branched pentyl, n-hexyl, or branched hexyl. In some embodiments, R$^{3b}$ is methyl.

In some embodiments, R¹ and R² are both chloro. In some embodiments, R¹ and R² are both chloro, and R³ is —OH.

In some embodiment, R¹ and R² are both chloro, R³ is —NHR$^{3b}$, and R$^{3b}$ is C$_{1-6}$ alkyl. R$^{3b}$ can be, for example, methyl, ethyl, n-propyl, isopropyl, n-butyl, isobutyl, sec-butyl, tert-butyl, n-pentyl, branched pentyl, n-hexyl, or branched hexyl. In some embodiments, R$^{3b}$ is methyl.

In some embodiments, the invention provides compounds of the structure:

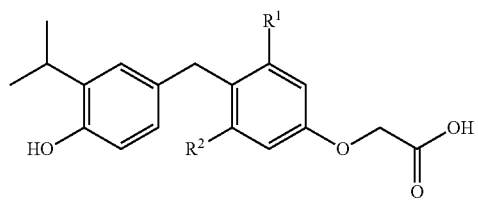

or any pharmaceutically acceptable salt thereof where R¹ and R² are both halo (including fluoro, bromo, chloro, or iodo). In some embodiments, R¹ and R² are both bromo. In some embodiments, R¹ and R² are both chloro. In some embodiments, R¹ is bromo and R² is chloro. In some embodiments, R¹ is chloro and R$_2$ is bromo.

While GC-1 was designed as a cardiac-sparing treatment for hypercholesterolemia by activating TRβ in the liver, recent studies have demonstrated its potential in demyelinating diseases ranging from multiple sclerosis (Baxi E G et al. *Glia* 62, 1513-1529 (2014); incorporated by reference herein) to X-linked adrenoleukodystrophy (Hartley, M. D. et al. *Endocrinology* 158, 1328-1338 (2017); Genin E C et al. *J Steroid Biochem Mol Biol* 116, 37-43 (2009); both of which are incorporated by reference herein). Despite these promising results, the effectiveness of GC-1 in treating demyelination is potentially limited by low brain uptake (Trost et al. 200 supra) and reduced receptor activation compared to thyroid hormone T3 (i.e., triiodothyronine; (2S)-2-amino-3-[4-(4-hydroxy-3-iodo-phenoxy)-3,5-diiodo-phenyl]propanoic acid). While many of the structural features of GC-1 are critical for its binding affinity and receptor selectivity, Yoshihara et al. 2003 supra) the 3,5-dimethyl constituents are not optimal. There is a large body of structure-activity relationship and quantitative structure-activity relationship data demonstrating that thyromimetics with inner ring methyl substitutions have significantly reduced activity in comparison to structurally similar analogs with inner ring halogen substitutions.

The iodine-free analog 3'-isopropyl-3,5-dibromo-L-thyronine (DIBIT) was 2- to 7-fold more potent than L-T4 in rat heart rate elevation and anti-goiter assays (Taylor R E et al. *Endocrinology* 80, 1143-1147 (1967); incorporated by reference herein) while the halogen-free analog 3'-isopropyl-3,5-dimethyl-DL-thyronine (DIMIT) had little measurable activity in the same assays (Jorgensen E C and Wright J, *J Med Chem* 13, 745-747 (1970); incorporated by reference herein). For the TRα-selective compounds CO22 and CO24, replacement of inner ring methyl groups with bromines improved binding affinity by 15-fold (Ocasio C A and Scanlan T S, *ACS Chem Biol* 1, 585-593 (2006) and Ocasio C A and Scanlan T S, *Bioorg Med Chem* 16, 762-770 (2008); both of which are incorporated by reference herein).

Scheme 1. Chemical structures of TR agonists

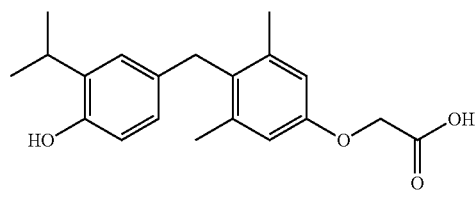

GC-1

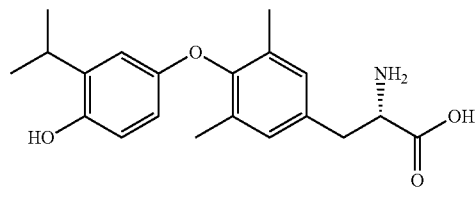

DIMIT

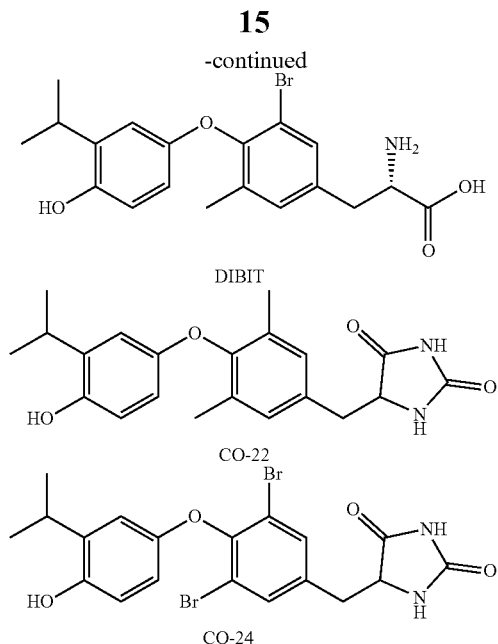

DIBIT

CO-22

CO-24

A QSSR study of thyroid hormone analogs suggested a mechanism for these findings—inner ring halogens can form a dipole-dipole interaction with a backbone carbonyl in the TR ligand binding domain, which influences binding affinity and selectivity (Valadares N F et al. *J Chem Inf Model* 49, 2606-2616 (2009); incorporated by reference herein). These data suggest that GC-1 could be improved by synthesizing new analogs that replace the inner ring methyl groups with halogens.

Replacing the inner ring methyl groups of GC-1 with halogens required a new synthetic approach. Work described in Dabrowski M et al. *Tetrahedron Letters* 46, 4175-4178 (2005), which is incorporated by reference herein, provided a template for producing the necessary 4-hydroxy-2,6-dihalobenzaldehyde intermediates by selective deprotonation of the 4-position of silyl protected 3,5-dihalophenols with lithium amide reagents. The method was improved by replacing the methyl ether and trimethylsilyl ether protecting groups used by Dabrowski with the more sterically bulky triethylsilyl ether protecting group, which significantly improved the selectivity of the deprotonation. These intermediates were used in a slightly altered version of the GC-1 synthesis reported in Placzek A T and Scanlan T S, *Tetrahedron* 71, 5946-5951 (2015); which is incorporated by reference herein. The 4-hydroxy-2,6-dihalobenzaldehyde intermediates could not be alkylated with tertbutyl chloroacetate using the standard cesium carbonate/DMF conditions due to the halogen substitutions reducing the nucleophilicity of the phenol. However, the reaction went to completion and in good yield after converting the alkyl chloride into an alkyl iodide via an in situ Finklestein reaction.

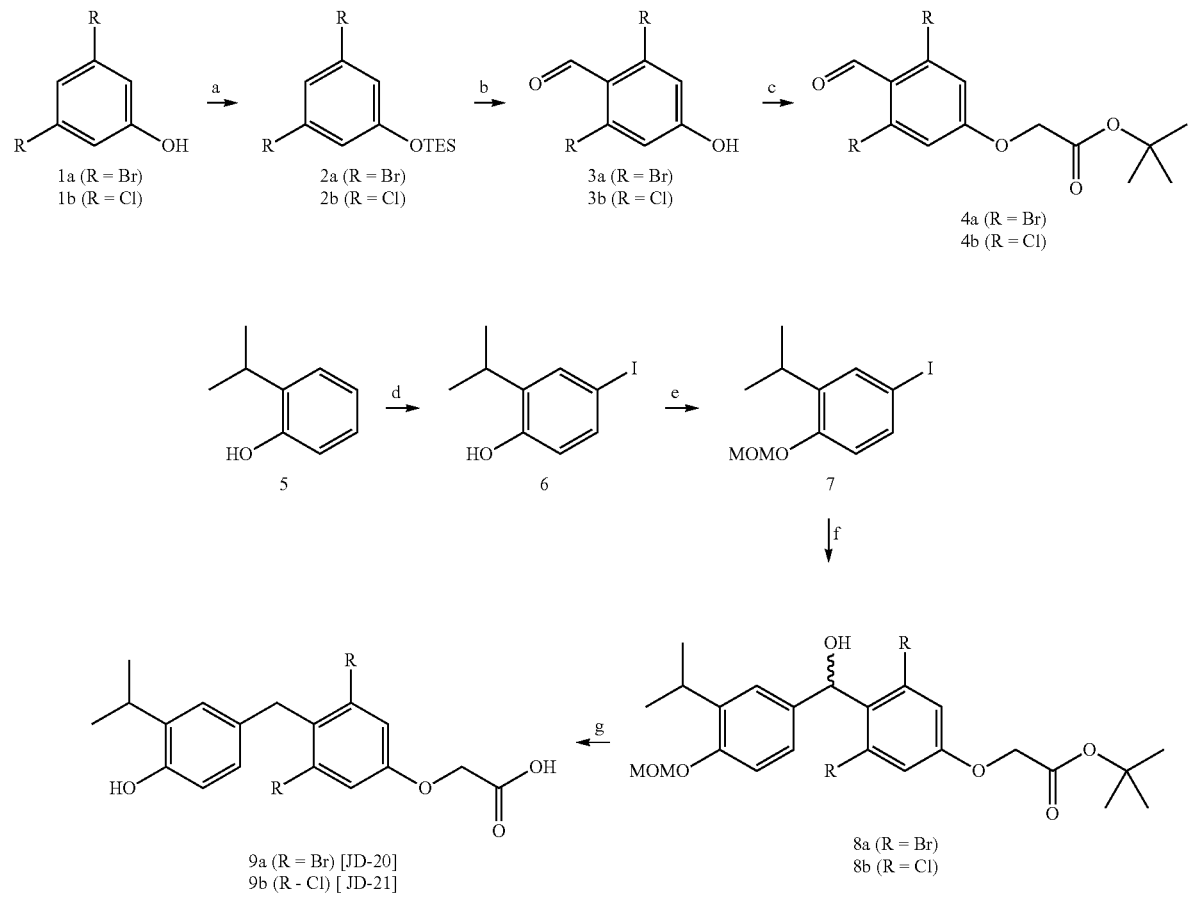

Scheme 2. Synthesis of JD-20 (9a) and JD-21 (9b)

Reagents and Conditions: (a) triethylsilyl chloride, imidazole, DCM, 0° C., 95%; (b) (i) nBuLi, DIA/TMP, THF, −78° C. (ii) DMF, 56-67%; (c) tertchloroacetate, NaI, Cs2CO3, acetone, 60-65° C., 84-88%; (d) NaI, NaOH, NaOCl, MeOH, H$_2$O, 87% (e) MOMCl, TBAI, NaOH, DCM, H2O, 81%; (f) (i) iPMgCl, THF, 0° C. to RT (ii) 4, −78° C., 54-79%; (g) TFA, triethylsilane, DCM, 0° C. to RT, 58-69%.

After forming the tert-butyl oxyacetate intermediate, the carbon-carbon bond formation proceeded in the same fashion as with GC-1 by forming an arylmagnesium with 7 that attacked the benzaldehyde to form a carbinol intermediate. The arylmagnesium nucleophile will not likely exchange with aryl chlorides or bromides at cryogenic temperatures and is compatible with the tert-butyl ester protecting group. Reduction of the carbinol and deprotection of the tert-butyl ester and methoxymethyl ether protecting groups proceeded simultaneously with TFA and triethylsilane in dichloromethane. The dibromo analog JD-20 was synthesized in 27% overall yield and the dichloro analog JD-21 was synthesized in 17% yield, both in five steps.

III. Pharmaceutical Compositions

The compounds disclosed herein may be included in pharmaceutical compositions (including therapeutic and prophylactic formulations), typically combined together with one or more pharmaceutically acceptable carriers (known equivalently as vehicles) and, optionally, other therapeutic ingredients.

Such pharmaceutical compositions can be formulated for administration to subjects by a variety of mucosal administration modes, including by oral, rectal, intranasal, intrapulmonary, intravitrial, or transdermal delivery, or by topical delivery to other surfaces including the eye. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other examples, the compound can be administered ex vivo by direct exposure to cells, tissues or organs originating from a subject.

To formulate the pharmaceutical compositions, the compound can be combined with various pharmaceutically acceptable additives. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween®-80), solubility enhancing agents (for example, cyclodextrins and derivatives thereof), stabilizers (for example, serum albumin), and reducing agents (for example, glutathione) can be included.

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7. The compound can be dispersed in any pharmaceutically acceptable carrier, which can include a hydrophilic compound having a capacity to disperse the compound, and any desired additives. The carrier can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a carrier, for example, polylactic acid, poly(lactic acid-glycolic acid) copolymer, polyhydroxybutyric acid, poly(hydroxybutyric acidglycolic acid) copolymer and mixtures thereof.

Alternatively or additionally, synthetic fatty acid esters such as polyglycerin fatty acid esters, sucrose fatty acid esters and the like can be employed as carriers. Hydrophilic polymers and other vehicles can be used alone or in combination, and enhanced structural integrity can be imparted to the vehicle by partial crystallization, ionic bonding, cross-linking and the like. The carrier can be provided in a variety of forms, including fluid or viscous solutions, gels, pastes, powders, microspheres, and films for direct application to a mucosal surface.

The compound can be combined with the carrier according to a variety of methods, and release of the compound can be by diffusion, disintegration of the vehicle, or associated formation of water channels. In some circumstances, the compound is dispersed in microcapsules (microspheres) or nanoparticles prepared from a suitable polymer, for example, 5-isobutyl 2-cyanoacrylate (see, for example, Michael et al. *J. Pharmacy Pharmacol.* 43, 1-5, (1991), and dispersed in a biocompatible dispersing medium, which yields sustained delivery and biological activity over a protracted time.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acidco-glycolic acid), poly(D-lactic acid-co-glycolic acid), and poly(L-lactic acid-coglycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (betahydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, Sustained and Controlled Release Drug Delivery Systems, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

IV. Methods for Treating Neurogenerative Disorders

Disclosed herein are methods of treating a subject with a neurodegenerative disorder through administration of one or more of the disclosed compounds. The compounds can be administered by any appropriate route including orally, parenterally, or topically. In particular examples, sobetirome, or a pharmaceutically acceptable salt thereof, is administered orally. In certain examples, sobetirome, or a pharmaceutically acceptable salt thereof, is administered parenterally. In some embodiments, sobetirome, or a pharmaceutically acceptable salt thereof, is administered buccally, sublingually, sublabially, or by inhalation. In other embodiments, sobetirome, or a pharmaceutically acceptable salt thereof, is administered sublingually. In yet other embodiments, sobetirome, or a pharmaceutically acceptable salt thereof, is administered parenterally. In particular embodiments, sobetirome, or a pharmaceutically acceptable salt thereof, is administered intra-arterially, intravenously, intraventricularly, intramuscularly, subcutaneously, intraspinally, intraorbitally, intracranially or intrathecally.

The administration of a pharmaceutical composition comprising the disclosed compounds can be for prophylactic or therapeutic purposes. For prophylactic and therapeutic purposes, the treatments can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the treatments for viral infection can be provided as repeated doses within a prolonged prophylaxis or treatment regimen that will yield clinically significant results to alleviate one or more symptoms or detectable conditions associated with a neurodegenerative disorder.

An effective amount or concentration of the disclosed compounds may be any amount of a composition that alone, or together with one or more additional therapeutic agents, is sufficient to achieve a desired effect in a subject. The effective amount of the agent will be dependent on several factors, including, but not limited to, the subject being treated and the manner of administration of the therapeutic composition. In one example, a therapeutically effective amount or concentration is one that is sufficient to prevent advancement, delay progression, or to cause regression of a disease, or which is capable of reducing symptoms caused by any disease, including neurodegenerative disorders.

In one example, a desired effect is to reduce or inhibit one or more symptoms associated with a neurodegenerative disorder. The one or more symptoms do not have to be completely eliminated for the composition to be effective. For example, a composition can decrease the sign or symptom by a desired amount, for example by at least 20%, at least 50%, at least 80%, at least 90%, at least 95%, at least 98%, or even at least 100%, as compared to how the sign or symptom would have progressed in the absence of the composition or in comparison to currently available treatments.

The actual effective amount will vary according to factors such as the type of neurological disorder to be protected against/therapeutically treated and the particular status of the subject (for example, the subject's age, size, fitness, extent of symptoms, susceptibility factors, and the like) time and route of administration, other drugs or treatments being administered concurrently, as well as the specific pharmacology of treatments for viral infection for eliciting the desired activity or biological response in the subject. Dosage regimens can be adjusted to provide an optimum prophylactic or therapeutic response.

An effective amount is also one in which any toxic or detrimental side effects of the compound and/or other biologically active agent is outweighed in clinical terms by therapeutically beneficial effects. A non-limiting range for a therapeutically effective amount of treatments for viral infection within the methods and formulations of the disclosure is about 0.0001 μg/kg body weight to about 10 mg/kg body weight per dose, such as about 0.0001 μg/kg body weight to about 0.001 μg/kg body weight per dose, about 0.001 μg/kg body weight to about 0.01 μg/kg body weight per dose, about 0.01 μg/kg body weight to about 0.1 μg/kg body weight per dose, about 0.1 μg/kg body weight to about 10 μg/kg body weight per dose, about 1 μg/kg body weight to about 100 μg/kg body weight per dose, about 100 μg/kg body weight to about 500 μg/kg body weight per dose, about 500 μg/kg body weight per dose to about 1000 μg/kg body weight per dose, or about 1.0 mg/kg body weight to about 10 mg/kg body weight per dose.

Determination of effective amount is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art, including the EAE model of multiple sclerosis. Using such models, only ordinary calculations and adjustments are required to determine an appropriate concentration and dose to administer a therapeutically effective amount of the treatments for viral infection (for example, amounts that are effective to alleviate one or more symptoms of a neurodegenerative disorder).

V. Examples

The following examples are for illustration only. In light of this disclosure, those of skill in the art will recognize that variations of these examples and other examples of the disclosed invention be possible without undue experimentation.

Example 1. Materials and Methods

Transactivation Assay. Human epithelial kidney cells (HEK 293) were grown to 80% confluency in Dubelcco's modified Eagles 4.5 g/L glucose medium (high glucose DMEM) containing 10% fetal bovine serum, 50 units/mL penicillin and 50 μg/mL streptomycin. The cells were trypsinized with 0.25% trypsin, then diluted to $5 \times 10^5$ cells/mL with high glucose DMEM. Cells were added to Costar 3917 96-well plates at $5 \times 10^4$ cells/well, then incubated at 37° C. for 24 hours. 1.5 μg of TR expression vector (full length TRα-CMV or TRβ-CMV), 1.5 μg of a reporter plasmid containing a DR4 thyroid hormone response element (TRE) direct repeat spaced by four nucleotides (AGGTCAcaggAGGTCA) cloned upstream of a minimal thymidine kinase promoter linked to a firefly luciferase coding sequence, and 0.75 μg of a pRL-SV40 constitutive Renilla luciferase reporter plasmid were diluted into 540 μl of OptiMEM. 27 μL of lipofectamine reagent was diluted into 540 μL of OptiMEM. The plasmid and lipofectamine dilutions were combined then incubated at RT for 10 min. The mixture was then diluted into 4.29 mL of OptiMEM. Plates were washed with 100 μL of phosphate buffered saline (PBS) at pH 7.2 without magnesium or calcium chloride per well. Transfection mixtures were added at 50 μL per well, then incubated at 37° C. for 4 hours. Modified DME/F-12 Ham's medium without phenol red containing 15 mM HEPES and bicarbonate, 5 mM L-glutamine, charcoal-stripped FBS, 50 units/mL penicillin and 50 μg/mL streptomycin was added at 50 μL per well, then the plates were incubated at 37° C. for 20 hours. Drug stocks were made at 10 mM in DMSO, then serially diluted to 1× concentrations in DME/F-12 Ham's. Plates were washed with 100 μL of PBS (pH 7.2) per well. 100 μL of each drug stock was added to the wells in triplicate, and then the plates were incubated at 37° C. for 24 hours.

Cells were assayed for luciferase activity using the Promega DualGlo kit. 50 μl of Luciferase Reagent were added per well, the plate was rocked for 15 min at RT, and then the plate was read for firefly luciferase activity. A 50 μl volume of Stop & Glo Reagent was added per well, then the plate was read for Renilla luciferase activity. Data normalized to Renilla internal control were analyzed with GraphPad Prism v.4a using the sigmoid dose response model to generate $EC_{50}$ values±SEM.

Animal Studies.

Experimental protocols were in compliance with the National Institutes of Health Guide for the Care and Use of Laboratory Animals and approved by the Oregon Health & Science University Institutional Animal Care & Use Committee. Wild type male C57BL/6J mice, aged 8-10 weeks, were housed in a climate controlled room with a 12 hour light-dark cycle with ad libitum access to food and water.

Distribution Studies.

Mice were injected once intraperitoneally (ip) with GC-1 at 9.14 μmol/kg, and analogs at 0.914, 9.14, and 30.5 μmol/kg. Euthanasia was performed on three mice per dose at 1 hr and the tissues and blood were harvested. Tissues were immediately frozen and blood was kept on ice for a minimum of 30 minutes and then spun down at 7,500×G for 15 minutes. Serum (100 uL) was collected and was stored with tissues at −80° C. until samples were processed.

Serum Processing.

The serum samples were warmed to RT and 10 uL of 2.99 μM internal standard (D6-GC-1) was added to them. Acetonitrile (500 uL) was added and the sample was vortexed for 20 seconds. The sample was then centrifuged at 10,000×G for 15 minutes at 4° C. Next, 90% of the upper supernatant was transferred to a glass test tube and concentrated using a speedvac for 1.5 hr at 45° C. The dried sample was then dissolved in 400 μL of 50:50 ACN:H2O and vortexed for 20 seconds. The resulting mixture was transferred to an Eppendorf tube and centrifuged at 10,000×G for 15 minutes. The supernatant was filtered with 0.22 04 centrifugal filters and submitted for LCMS/MS analysis. The standard curve was made with 100 μL of serum from a 8-10 week old mouse not injected with T3, GC-1, or analogs. The processing was performed exactly the same except after filtering the sample was split among 6 vials. GC-1, JD-20, and JD-21 were added to 5 of the 6 vials to make final concentrations of each compound in matrix of (0.1 pg/μL, 1 pg/μL, 10 pg/μL, 100 pg/μL, and 1000 pg/μL).

Brain Processing.

The brain samples were warmed to RT and transferred to a homogenizer tube with 5 GoldSpec ⅛ chrome steel balls (Applied Industrial Technologies). The resulting tube was weighed and then 1 mL of H2O was added, followed by 10 μL, of 2.99 μM internal standard (D6-Sobetirome). The tube was homogenized with a Bead Bug for 30 seconds and then transferred to a Falcon® tube containing 3 mL of ACN. A 1 ml volume of ACN was used to wash the homogenizer tube. Then the solution was transferred back to the Falcon® tube. The sample was then processed using the same method for the serum processing described above except the sample was concentrated in a glass tube using a speed vac for 4 hr at 45° C.

Gene Activation.

Mice were injected once intraperitoneally (ip) with vehicle (1:1 saline/DMSO), T3 at 0.305 μmol/kg, GC-1 at 9.14 μmol/kg, and analogs at 0.914, 9.14, and 30.5 μmol/kg. Euthanasia was performed on three mice per dose at 2 hr and the tissues were harvested. The brain tissues collected for qPCR analysis were processed according to a protocol for RNA extraction using Trizol reagent and the PureLink RNA mini kit, using Qiagen RNase-free DNase kit during the optional DNase treatment step. 1 μg of extracted RNA was used to synthesize cDNA via a reverse transcription (RT) reaction using the Qiagen QuantiTect Reverse Transcription kit. DNA contamination was controlled for by duplicating one sample without the addition of RT enzyme. Expression of the Hairless (Hr) gene was measured by QPCR using the QuantiTect SYBR green PCR kit from Qiagen. The primer sequences for hairless (Fwd: CCAAGTCTGGGC-CAAGTTTG; Rev: TGTCCTTGGTCCGATTGGAA) were previously described by Barca-Mayo19. The template cDNA was diluted 2-fold to minimize the interference of RT reagents in the qPCR reaction. Glyceraldehyde-3-Phosphate Dehydrogenase (GAPDH) was the housekeeping gene used for normalizing between samples. Data analysis for single dose experiment was done using the comparative CT method to look at the relative differences in Hr gene expression. Data analysis for dose-response experiment was done using GraphPad Prism v.4a with the sigmoid dose response model to generate $EC_{50}$ values±SEM.

Chemistry General.

$^1$H NMR were taken on a Bruker 400. All $^1$H NMR were calibrated to the NMR solvent reference peak (D6-acetone, CDCl3). Anhydrous tetrahydrofuran (THF) and dimethylformamide (DMF) were obtained from a Seca Solvent System. All other solvents used were purchased from Sigma-Aldrich or Fisher. Purity analysis of final compounds was determined to be >95% by HPLC. HPLC analysis was performed on a Varian ProStar HPLC with an Agilent Eclipse Plus C18 5 μM column (4.6×250 mm) with a gradient of 10% to 95% acetonitrile (0.1% TFA) over 15 minutes.

Example 2. Preparation of
(3,5-Dibromophenoxy)Triethylsilane (2a)

1a (5.04 g, 20 mmol) and imidazole (4.09 g, 60 mmol) were dissolved in 80 mL of DCM. The solution was cooled to 0° C., then triethylsilyl chloride (5.03 mL, 30 mmol) was added, then the reaction was stirred at 0° C. for 30 min. The reaction was diluted with 160 mL of Et2O, washed 2× with 50 mL of H2O and 2× with 50 mL of brine, then dried with $MgSO_4$, filtered, and concentrated to give the 2a in quantitative yield, which was used without purification. $^1$H NMR (400 MHz, CDCl3): δ 7.37 (t, 1H), 7.10 (d, 2H), 1.02 (t, 9H), 0.82 (q, 6H).

Example 3. Preparation of
4-Hydroxy-2,6-Dibromobenzaldehyde (3a)

A flask was loaded with molecular sieves, then flame-dried under vacuum. After cooling under argon, 2a (5.49 g, 15 mmol) was loaded, then the flask was sealed, evacuated, and flushed with argon. 30 mL of dry THF were added and degassed, then the solution was cooled to −78° C. A second flask was loaded with molecular sieves, then flame-dried under vacuum. After cooling under argon, diisopropylamine (4.6 mL, 33 mmol) was added, followed by 60 mL of dry THF, then the solution was degassed and cooled to −78° C. 2.5 M n-butyllithium solution in hexanes (12 mL, 30 mmol) was added, then the solution was stirred for 1 hr at −78° C. The lithium diisopropylamide solution was transferred dropwise via cannula to the 2a solution, then the deprotonation was stirred for 1 hr at −78° C. 5.8 mL of dry DMF (75 mmol) were added, then the reaction was stirred for 1 hr at −78° C. The reaction was decanted into 50 mL of 1 N aqueous HCl. The aqueous layer was extracted 3× with 90 mL of $Et_2O$. The organic fractions were combined, washed 2× with 50 mL of brine, then dried with $MgSO_4$, filtered, and concentrated to give the crude product, which was precipitated from hexanes at −78° C. to give 2.8 g of 3a (67% yield). $^1$H NMR (400 MHz, d6-acetone) δ 10.16 (s, 1H), 7.27 (s, 2H).

Example 4. Preparation of Tert-Butyl
2-(3,5-Dibromo-4-Formylphenoxy)Acetate (4a)

3a (2.8 g, 10 mmol), sodium iodide (3 g, 20 mmol), and cesium carbonate (3.24 g, 10 mmol) were dissolved in 40 mL of acetone. 2.86 mL tert-butyl chloroacetate (20 mmol) were added, then the reaction was refluxed at 65° C. for 2 hr. The reaction was diluted with 80 mL of $Et_2O$, washed 2× with 30 mL of water and 2× with 30 mL of brine, then dried with $MgSO_4$, filtered, and concentrated. The product was precipitated from hexanes and collected by filtration, then dried under vacuum to give 3.49 g of 4a (88% yield). $^1$H NMR (400 MHz, $CDCl_3$) δ 10.23 (s, 1H), 7.19 (s, 2H), 4.59 (s, 2H), 1.52 (s, 9H).

Example 5. Preparation of
(3,5-Dichlorophenoxy)Triethylsilane (2b)

1b (6.54 g, 40 mmol) and imidazole (8.18 g, 120 mmol) were dissolved in 160 mL of DCM. The solution was cooled to 0° C., then triethylsilyl chloride (10 mL, 60 mmol) was added, then the reaction was stirred at 0° C. for 30 min. The reaction was diluted with 320 mL of $Et_2O$, washed 2× with 100 mL of H2O and 2× with 75 mL of brine, then dried with $MgSO_4$, filtered, and concentrated to give 2b, which was used without purification and weighed 10.58 g after drying (95% yield). $^1$H NMR (400 MHz, $CDCl_3$) δ 6.98 (t, 1H), 6.76 (d, 2H), 1.02 (t, 9H), 0.77 (q, 6H).

Example 6. Preparation of
4-Hydroxy-2,6-Dichlorobenzaldehyde (3b)

A flask was loaded with molecular sieves, then flame-dried under vacuum. After cooling under argon, 2b (3.6 g, 13 mmol) was loaded, then the flask was sealed, evacuated, and flushed with argon. 13 mL of dry THF were added and degassed, then the solution was cooled to −78° C. A second flask was loaded with molecular sieves, then flame-dried under vacuum. After cooling under argon, 2,2,6,6-tetramethylpiperdidine (1.84 g, 13 mmol) was added, followed by 13 mL of dry THF, then the solution was degassed and cooled to −78° C. 2.5 M n-butyllithium solution in hexanes (5.2 mL, 13 mmol) was added, then the solution was stirred for 20 min at 0° C. The lithium TMP solution was transferred dropwise via cannula to the 2b solution, then the deprotonation was stirred for 30 min at −78° C. 5 mL of dry DMF (65 mmol) were added, then the reaction was stirred for 30 min at −78° C. The reaction was decanted into 15 mL of 1 N aqueous HCl. The aqueous layer was extracted 3× with 15 mL of EtOAc. The organic fractions were combined, washed 2× with 15 mL of brine, then dried with MgSO4, filtered, and concentrated to give the crude product, which was recrystallized from hexanes at −20° C. to give 1.39 g of 3b (56% yield). $^1$H NMR (400 MHz, d6-acetone) δ 10.37 (s, 1H), 7.01 (s, 2H).

Example 7. Preparation of Tert-Butyl 2-(3,5-Dichloro-4-Formylphenoxy)Acetate (4b)

3b (1.15 g, 6 mmol), sodium iodide (1.8 g, 12 mmol), and cesium carbonate (1.94 g, 6 mmol) were dissolved in 24 mL of acetone. 1.72 mL tert-butyl chloroacetate (12 mmol) were added, then the reaction was refluxed at 60° C. for 24 hr. The reaction was diluted with 30 mL of $Et_2O$, washed 2× with 10 mL of water and 2× with 10 mL of brine, then dried with MgSO4, filtered, and concentrated. The crude oil was redissolved in a minimal amount of $Et_2O$ then added dropwise to 100 mL of vigorously stirring hexanes at −78° C. The precipitate was collected by filtration and dried under vacuum to give 1.545 g of 4b (84% yield). $^1$H NMR (400 MHz, $CDCl_3$) δ 10.43 (s, 1H), 6.92 (s, 2H), 4.59 (s, 2H), 1.52 (s, 9H).

Example 8. Preparation of 4-Iodo-2-Isopropylphenol (6)

5 (6.8 g, 50 mmol) and NaI (7.5 g, 50 mmol) were dissolved in 70 mL of MeOH. 10 M aqueous NaOH (5 mL, 50 mmol) was added, then the solution was cooled to 0° C. 6.25% w/v aqueous NaOCl (62.5 mL, 50 mmol) was added drop wise over 24 hr at 0° C. The reaction was acidified to pH 7 with 12 N aqueous HCl, then quenched with 10 mL of saturated aqueous $Na_2S_2O_3$. The aqueous layer was extracted 3× with $Et_2O$. The organic fractions were combined, washed 2× with brine, then dried with MgSO4, filtered, and concentrated to give the crude product, which was purified by flash chromatography (silica gel, hexane/ethyl acetate, 1-20%) to give 11.35 g of 6 (87% yield) as a reddish oil. $^1$H NMR (400 MHz, CDCl3) δ 7.47 (d, 1H), 7.36 (dd, 1H), 6.54 (d, 1H), 3.16 (m, 1H), 1.25 (d, 6H).

Example 9. Preparation of 4-Iodo-2-Isopropyl-1-(Methoxymethoxy)Benzene (7)

6 (2.62 g, 10 mmol) and tetrabutylammonium iodide (369 mg, 1 mmol) were dissolved in 100 mL of DCM. 10 mL of 10 M aqueous NaOH were added, followed by 5 mL of 6 M chloromethyl methyl ether in MeOAc. The reaction was stirred for 30 min at RT, then diluted with 200 mL of $Et_2O$. The organic layer was washed 2× with 100 mL of $H_2O$ and 2× with 100 mL of brine, then dried with MgSO4, filtered, and concentrated to give the crude product, which was purified by flash chromatography (silica gel, hexane/ethyl acetate, 1-20%) to give 2.48 g of 7 (81% yield). $^1$H NMR (400 MHz, CDCl3) δ 7.47 (d, 1H), 7.42 (dd, 1H), 6.83 (d, 1H), 5.18 (s, 2H), 3.47 (s, 3H), 3.27 (m, 1H), 1.20 (d, 6H).

Example 10. Preparation of Tert-Butyl 2-(3,5-Dibromo-4-(Hydroxy(3-Isopropyl-4-(Methoxymethoxy)Phenyl) Methyl)Phenoxy)Acetate (8a)

A flask was loaded with 4 Å molecular sieves and flame-dried under vacuum. 7 (1.47 g, 4.8 mmol) was loaded and the flask was sealed, evacuated, and flushed with argon. 24 mL of dry THF were added and degassed, then the solution was cooled to 0° C. Isopropylmagnesium chloride (2 M THF, 5.5 mL, 7.2 mmol) was added, then the reaction was stirred for 2 hours at RT. A second flask was loaded with 4 Å molecular sieves and flame-dried under vacuum. 4a (946 mg, 2.4 mmol) was loaded and the flask was sealed, evacuated, and flushed with argon. 12 mL of dry THF were added and degassed. The arylmagnesium solution was cooled to −78° C., then the 4a solution was added drop wise via cannula and the reaction was stirred for 1 hour at −78° C. The reaction was quenched with 10 mL of 1 N aqueous HCl. The aqueous layer was extracted 3× with 10 mL of EtOAc. The organic fractions were combined and washed 2× with 10 mL of brine. The organic layer was dried with MgSO4, filtered, and concentrated to give the crude product, which was purified by flash chromatography (silica gel, hexanes/EtOAc 4-40%) to give 1.089 g of 8a (79% yield). $^1$H NMR (400 MHz, CDCl3) δ 7.24 (d, 1H), 7.17 (s, 2H), 7.00 (d, 1H), 6.90 (dd, 1H), 6.51 (d, 1H), 5.21 (s, 2H), 4.53 (s, 2H), 3.49 (s, 3H), 3.34 (m, 3H), 1.52 (s, 9H), 1.21 (t, 6H).

Example 11. Preparation of 2-(3,5-Cibromo-4-((3-Isopropyl-4-Hydroxyphenyl)Methyl)-Phenoxy)Acetic Acid (9a)

8a (1.089 g, 1.9 mmol) was dissolved in 19 mL of DCM with 1.21 mL of triethylsilane (7.58 mmol). The solution was cooled to 0° C., then 4.35 mL of trifluoroacetic acid (56.9 mmol) were added and the reaction was stirred for 30 min at 0° C., then 2 hr at RT. Solvent was removed under vacuum, then the product was precipitated by the addition of hexanes and collected by filtration. The solid was dried under vacuum to give 505 mg of JD-20 (9a) (58% yield). $^1$H NMR (400 MHz, CDCl3) δ 7.19 (s, 2H), 7.10 (d, 1H), 6.82 (dd, 1H), 6.64 (d, 1H), 4.68 (s, 2H), 4.28 (s, 2H), 3.18 (m, 1H), 1.24 (d, 6H).

Example 12. Preparation of Tert-Butyl 2-(3,5-Dichloro-4-(Hydroxy(3-Isopropyl-4-(Methoxymethoxy)Phenyl) Methyl)Phenoxy)Acetate (8b)

A flask was loaded with 4 Å molecular sieves and flame-dried under vacuum. 7 (459 mg, 1.5 mmol) was loaded and the flask was sealed, evacuated, and flushed with argon. 6 mL of dry THF were added and degassed, then the solution was cooled to 0° C. Isopropylmagnesium chloride (2 M THF, 1.125 mL, 2.25 mmol) was added, then the reaction was stirred for 2 hours at RT. A second flask was loaded with 4 Å molecular sieves and flame-dried under vacuum. 4b (305 mg, 1 mmol) was loaded and the flask was sealed, evacuated, and flushed with argon. 4 mL of dry THF were added and degassed. The arylmagnesium solution was cooled to −78° C., then the 4b solution was added drop wise via cannula and the reaction was stirred for 1 hour at −78° C. The reaction was quenched with 5 mL of 1 N aqueous HCl. The aqueous layer was extracted 3× with 5 mL of EtOAc. The organic fractions were combined and washed 2× with 5 mL of brine. The organic layer was dried with MgSO4, filtered, and concentrated to give the crude product, which was purified by flash chromatography (silica gel, hexanes/EtOAc 2-20%) to give 260 mg of 8b (54% yield). $^1$H NMR (400 MHZ, CDCl3) δ 7.26 (d, 1H), 6.99 (dd, 1H), 6.94 (d, 1H), 6.93 (s, 2H), 6.50 (d, 1H), 5.21 (s, 2H), 4.53 (s, 2H), 3.50 (s, 3H), 3.33 (m, 1H), 3.23 (d, 1H), 1.52 (s, 9H), 1.21 (t, 6H).

Example 13. Preparation of 2-(3,5-Dichloro-4-((3-Isopropyl-4-Hydroxyphenyl)Methyl)-Phenoxy)Acetic Acid (9b)

8b (260 mg, 0.54 mmol) was dissolved in 5.4 mL of DCM with 0.345 mL of triethylsilane (2.16 mmol). The solution was cooled to 0° C., then 1.24 mL of trifluoroacetic acid (16.2 mmol) were added and the reaction was stirred for 30 min at 0° C., then 2 hr at RT. Solvent was removed under vacuum, then the product was precipitated by the addition of hexanes and collected by filtration. The solid was dried under vacuum to give 137 mg of JD-21 (9b) (69% yield). $^1$H NMR (400 MHz, CDCl3) δ 7.12 (d, 1H), 6.95 (s, 2H), 6.86 (dd, 1H), 6.64 (d, 1H), 4.68 (s, 2H), 4.18 (s, 2H), 3.17 (m, 1H), 1.24 (d, 6H).

Example 14. Biological Activity of Halogenated Compounds

Figure 1B:
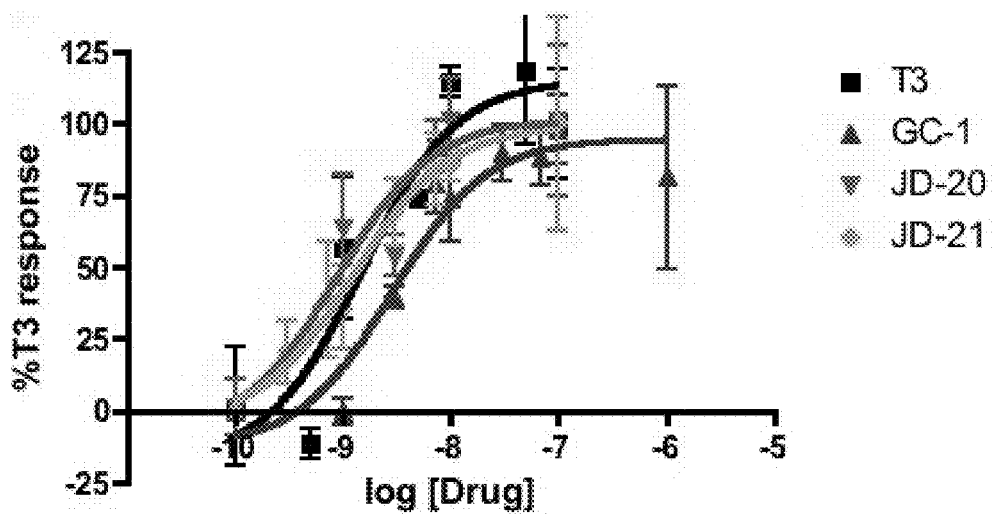
FIG. 1B is a plot of the data from a TRE-driven dual luciferase transactivation assays with calculated sigmoidal dose-response curves against hTRβ1 in transiently transfected HEK293 cells. Plots show means of triplicates with error bars normalized to T3 response.

Cell-based in vitro transactivation assays show that JD-20 and JD-21 have improved potency in comparison to their parent GC-1 (FIG. 1). While increases in potency at TRα were modest, greater improvements were seen at TRβ, nearly matching the EC50 of T3 (Table 1).

TABLE 1

Subtype selectivity measured from EC50 values from TRE-driven dual luciferase transactivation assays.

| Compound | $EC_{50}$ TRα (nM) | $EC_{50}$ TRβ (nM) | TRβ/TRα |
|---|---|---|---|
| T3 | 1.01 ± 0.4 | 1.49 ± 1.57 | 0.678 |
| GC-1 | 74.7 ± 28.9 | 2.82 ± 1.81 | 26.5 |
| JD-20 | 7.96 ± 6.95 | 0.88 ± 1.12 | 9.04 |
| JD-21 | 7.82 ± 3.61 | 1.24 ± 1.30 | 6.31 |

Figure 2:
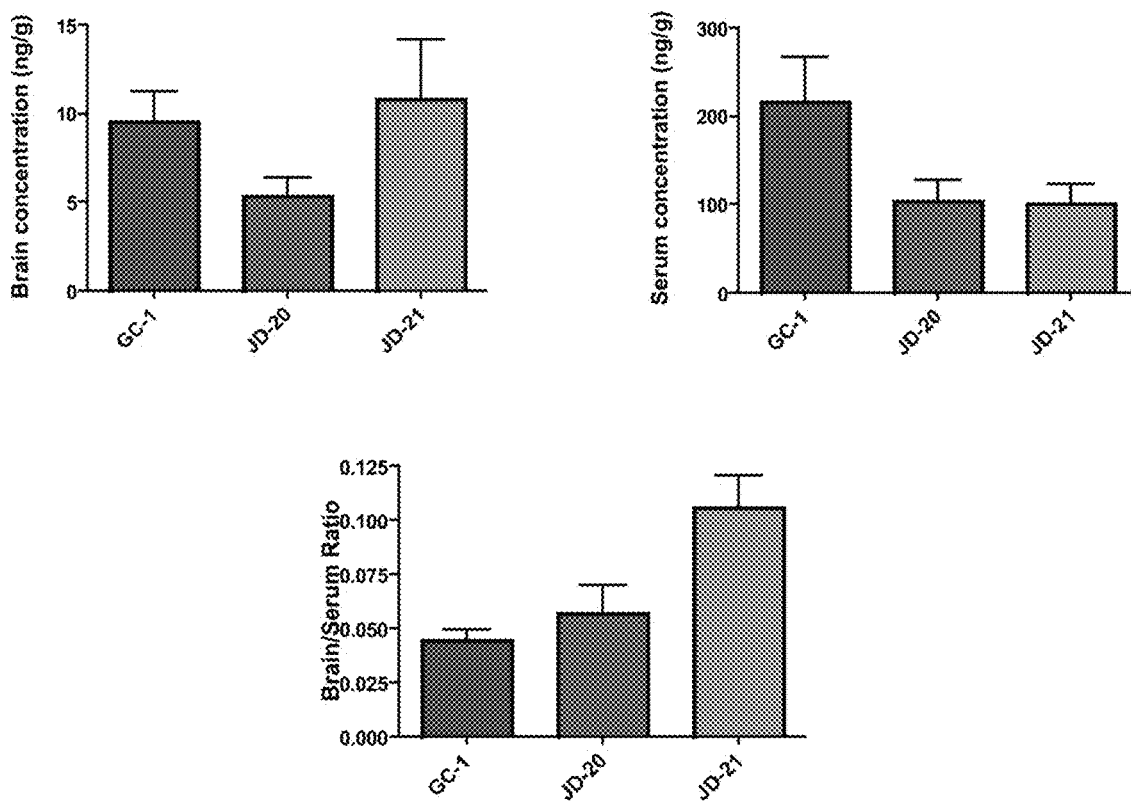
FIG. 2 is a set of three bar graphs showing in vivo concentrations of GC-1, JD-20, and JD-21 in C57/B mouse tissues 1 hr after systemic administration (ip) of GC-1, JD-20, and JD-21 9.14 μmol/kg doses measured by LC-MS/MS in brain and serum.

A distribution study was carried out in C57BL/6J mice to determine the concentrations in brain and serum after systemic (ip) administration. Mice were given single 9.14 μNmol/kg doses of GC-1, JD-20, or JD-21. Tissue and blood were collected 1 hr post-injection and the concentration of the drugs was determined by LC-MS/MS analysis (FIG. 2). JD-21 showed roughly comparable brain uptake compared to GC-1 while JD-20 was somewhat lower. The serum levels of JD-20 and JD-21 were both significantly lower than GC-1, combining to give JD-21 a higher brain: serum ratio than GC-1 while JD-20 had a brain: serum ratio comparable to GC-1.

Figure 3:
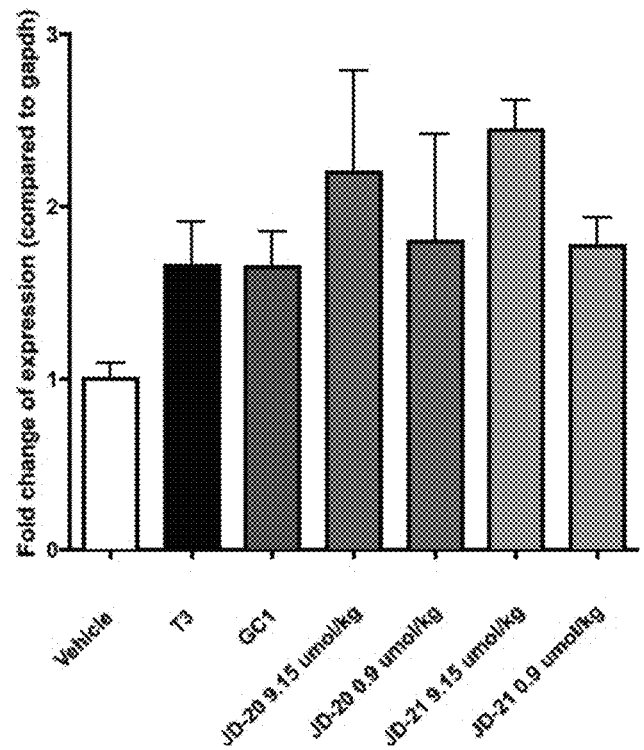
FIG. 3 is a bar graph showing expression of TR regulated gene Hairless (Hr) mRNA normalized to glyceraldehyde 3-phosphate dehydrogenase (GAPDH) mRNA measured by qPCR in C57/B mouse brain (3 mice/dose) 2 hr after systemic administration (ip) of saturating doses of T3 (0.305 μmol/kg) or GC-1 (9.14 μmol/kg) plus escalating doses of JD-20 and JD-21 (0.914 and 9.14 μmol/kg).

Induction of Hairless (Hr), a TR target gene, mRNA expression in the brain was determined by qPCR and normalized to glyceraldehyde 3-phosphate dehydrogenase (GAPDH) mRNA (FIG. 3). Vehicle (1:1 saline/DMSO) was used as a negative control and saturating doses of T3 (0.305 μmol/kg) and GC-1 (9.14 μmol/kg) were used as positive controls. JD-21 at 9.14 μmol/kg (2.4-fold) had significantly (p<0.05) greater induction of Hr expression in comparison to GC-1 at 9.14 μmol/kg (1.6-fold). JD-20 and JD-21 at 0.914 μmol/kg had comparable Hr induction to GC-1 at the same dose, suggesting roughly 10-fold greater potency than GC-1.

Figure 4:
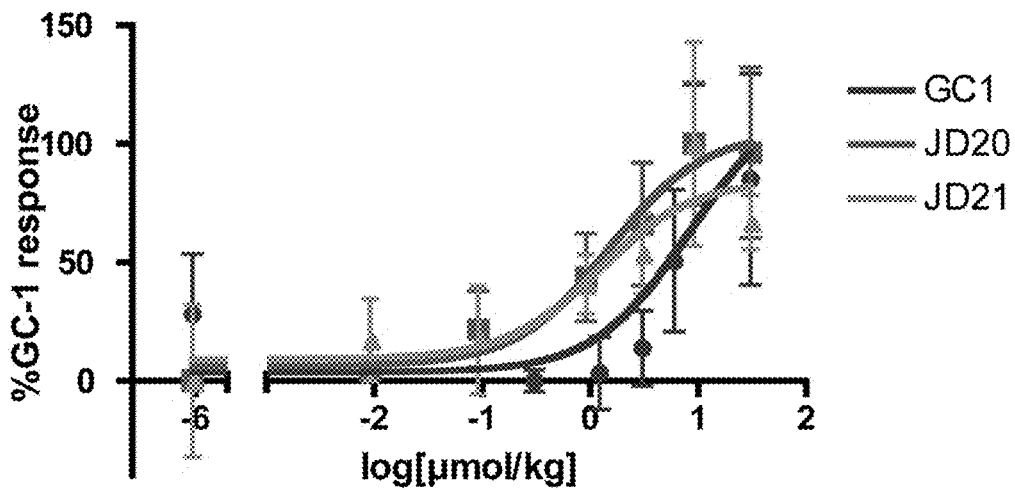
FIG. 4 is a plot of the expression of TR regulated gene Hairless (Hr) mRNA normalized to glyceraldehyde 3-phosphate dehydrogenase (GAPDH) mRNA measured by qPCR in C57/B mouse brain (3 mice/dose) 2 hr after systemic administration (ip) of GC-1, JD-20, and JD-21.

The $EC_{50}$ values of Hr mRNA induction in the brain normalized to GAPDH mRNA expression by GC-1, JD-20, and JD-21 (FIG. 4) were determined using the same experimental protocol. The EC50 for GC-1 was 8.20±12.65 μmol/kg, the EC50 for JD-20 was 1.49±1.08 μmol/kg, and the EC50 for JD-21 was 1.21±1.75 μmol/kg, making the halogenated analogs roughly 6-fold more potent than GC-1 at inducing Hr mRNA expression in the brain.

While GC-1 has become one of the standard TRβ-selective thyromimetics in the field, this study makes clear that replacing the inner ring methyl groups with a halogen produces significantly improved compounds that maintain critical properties of the parent. The TRβ-selectivity and CNS penetration of GC-1 are preserved in JD-20 and JD-21, suggesting that they should be effective in CNS indications.

The improved potency of JD-20 and JD-21 is consistent with numerous thyromimetic SAR studies that have found superior activity for analogs with halogens in the 3,5-position compared to similar analogs with methyl groups at those positions. What is surprising in this instance is that by most measures JD-20 and JD-21 appear to have very similar properties. In previous thyromimetic SAR studies changing halogens frequently produced dramatic changes in both potency and selectivity. On this scaffold the only major difference is found in brain uptake, where JD-20 has a reduced uptake in comparison to GC-1 and JD-21.

Example 15. Preparation of 2-(3, 5-dibromo-4-(4-hydroxy-3-isopropylbenzyl) phenoxy)-N-methylacetamide (MA-JD20, 10a)

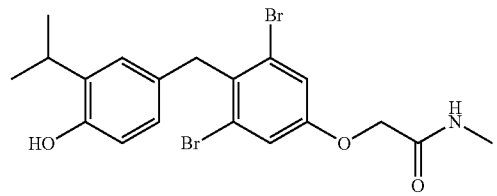

2-(3,5-dibromo-4-(4-hydroxy-3-isopropylbenzyl) phenoxy) acetic acid (100 mg, 0.22 mmol) was dissolved in methanol (4 mL) in a sealed tube and one drop of concentrated sulfuric acid was added to it. The sealed reaction mixture was heated to 65° C. with stirring for one hour. It was then cooled to room temperature and TLC (ethyl acetate: hexane 1:1) showed complete conversion to the corresponding methyl ester. To this solution was then added 40% methyl amine in water (285 μl, 3.3 mmol, 15 equiv.) and it was again heated to 65° C. for one hour in sealed condition. It was cooled and complete conversion to the product was observed by TLC. Sodium hydroxide (0.5N, 10 ml) was added to it and the product was extracted with dichloromethane (3×50 ml). The organic layers were combined, dried on anhydrous $Mg_2SO_4$, filtered and concentrated. The crude product was purified by flash chromatography (50% hexane in ethyl acetate). On recrystallization from a mixture of hexane and dichloromethane, the final compound was obtained (70 mg, 0.15 mmol, 68%). $^1$H NMR (400 MHz, MeOH-$d_4$): δ=7.35 (s, 2H), 6.98 (d, 1H, J=2.3 Hz), 6.74 (dd, 1H, J=8.3 Hz, 2.3 Hz), 6.62 (d, 1H, J=8.2 Hz), 4.55 (s, 2H), 4.26 (s, 2H), 3.24 (septet, 1H, J=6.9 Hz), 2.84 (s, 3H), 1.17 (d, 6H, J=6.98 Hz). HRMS exact mass calculated for $C_{19}H_{21}Br_2NO_3[M+H]^+$: m/z 471.99416, found m/z 471.99446.

Example 16. Preparation of 2-(3, 5-dichloro-4-(4-hydroxy-3-isopropylbenzyl) phenoxy)-N-methylacetamide (MA-JD21, 10b)

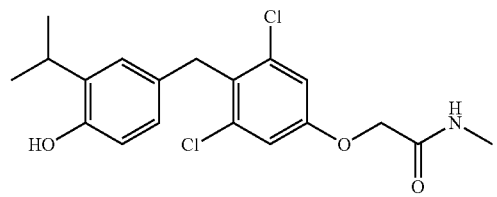 [SMILES: CNC(=O)COc1cc(Br)c(Cc2ccc(O)c(C(C)C)c2)c(Br)c1]

2-(3, 5-dichloro-4-(4-hydroxy-3-isopropylbenzyl) phenoxy) acetic acid (100 mg, 0.27 mmol, 1 equiv.) was dissolved in methanol (5 mL) in a sealed tube. Sulfuric acid (1 drop) added to it and the reaction was sealed and heated to 65° C. for one hour while stirring. It was cooled to room temperature and TLC analysis (ethyl acetate: hexane 1:1) shows complete conversion to the intermediate methyl ester. To this was then added 40% methyl amine in water (320 µl, 4 mmol, 15 equiv.). The reaction is resealed and heated to 65° C. for one hour. The reaction flask was cooled to room temperature and sodium hydroxide (0.5N, 10 mL) added to it. The reaction product was extracted with dichoromethane (3×50 mL). The organic layers were combined, dried on anhydrous $Mg_2SO_4$, filtered and concentrated. Purification by flash chromatography (50% hexane in ethylacetate) gave the product as a white solid (65 mg, 0.17 mmol, 63%). $^1$H NMR (400 MHz, MeOH-$d_4$): δ=7.12 (s, 2H), 7.01 (d, 1H, J=1.98 Hz), 6.77 (dd, 1H, J=8.21 Hz, 2.26 Hz), 6.62 (d, 1H, J=8.21 Hz), 4.56 (s, 2H), 4.15 (s, 2H), 3.23 (septet, 1H, J=7.14 Hz), 2.85 (s, 3H), 1.17 (d, 6H, J=6.93 Hz). HRMS exact mass calculated for $C_{19}H_{21}Cl_2NO_3$ [M+H]$^+$: m/z 384.09455, found m/z 384.09473.

Example 17. Biological Activity of Halogenated Amides

Animal Studies.

Wild type male C57Bl/6 mice, aged 8-10 weeks, were housed in a climate-controlled room with a 12 hour light-dark cycle with ad libitum access to food and water. To compare the single time-point drug distribution of JD-20 with JD-20 generated from the amide MA-JD20, and JD-21 with JD-21 generated from the amide MA-JD21, the concentrations of the parent drugs were analyzed in brain and serum of mice by administering a dose of 3.05 µmol/kg (three mice per dose) with JD-20, JD-21, MA-JD20 and MA-JD21 both intraperitoneally and orally. The compounds were dissolved in a mixture of 50:50 DMSO and 0.9% sodium chloride bacteriostatic solution. Oral gavage was performed with the use of plastic feeding tubes (20 ga×38 mm, Instech Laboratories Inc., PA, USA) connected to 500 µl insulin syringes (Covidien LLC MA, USA). In both experiments, the mice were euthanized after 1 hour following drug administration.

As a follow-up of the single time point study, a 24 h time course study through oral gavage was performed for the amides, MA-JD20 and MA-JD21, and the corresponding JD-20 or JD-21 concentrations were measured in brain and blood of mice. Pharmacokinetic time-course curves were generated from these analyses and area under the curve (AUC) values for brain and blood were obtained.

The tissues were processed as follows: The brains were collected in previously weighed homogenizer tubes with 3 Gold Spec ⅛ chrome steel balls (Applied Industrial Technologies) and immediately frozen at −80° C. The blood samples were kept on ice for 30 mins and then spun down at 5400×G at 4° C. for 15 min. Serum (100 µl) was collected from the top and stored at −80° C. until the samples were processed.

Serum Processing:

The serum samples were warmed to room temperature. Acetonitrile (500 µl) and the internal standard $d_6$-sobetirome (2.99 µM, 10 µl) were added to each sample and vortexed for 20 seconds. They were then centrifuged at 10,000×G for 15 minutes at 4° C. The supernatants were transferred to a set of labeled 13×100 mm borosilicate glass tubes and concentrated in the speedvac concentrator at 45° C. for 2 hours. The dried samples were then dissolved in 400 µl of a 50:50 mixture of acetonitrile and water and vortexed for 20 seconds. The resulting mixtures were transferred to Eppendorf tubes and centrifuged at 10,000×G for 15 minutes at 4° C. The serum samples thus prepared were submitted for LC-MS/MS analysis to quantify the amount of free JD-20 or JD-21.

The standard curve was made with 100 µl of serum collected from an 8-10 week old C57Bl/6 mouse that received vehicle only (a mixture of 50:50 DMSO and 0.9% sodium chloride bacteriostatic solution) injection. The serum sample was processed exactly the same way except after final centrifugation the sample was split into 6 vials. To 5 out of these 6 vials was added a mixture of JD-20 and JD-21 to make the concentration of each compound in matrix of (0.1ρg/µl, 1.0ρg/µl, 10ρg/µl/100ρg/µl and 1000ρg/µl).

Brain Processing:

The brain samples were warmed to room temperature and weighed. Water (1 ml) and the internal standard $d_6$-Sobetirome (2.99 µM, 10 µl) were added to each sample and vortexed for 20 seconds. They are homogenized in Omni Bead ruptor 24 for one minute and then transferred to labeled 15 ml Falcon tubes each containing 3 ml of acetonitrile. A 1 ml volume of acetonitrile was used to wash the homogenizer tube and the washing was added to the falcon tube. The tubes were vortexed for 20 seconds and centrifuged at a speed of 10,000×G for at 4° C. The supernatants from these tubes are carefully decanted into a set of labeled 13×100 mm borosilicate glass tubes and concentrated in the speedvac at 45° C. for 4 hours. The samples were then processed using the serum processing method for LC-MS/MS analysis.

Results.

Figure 5A:
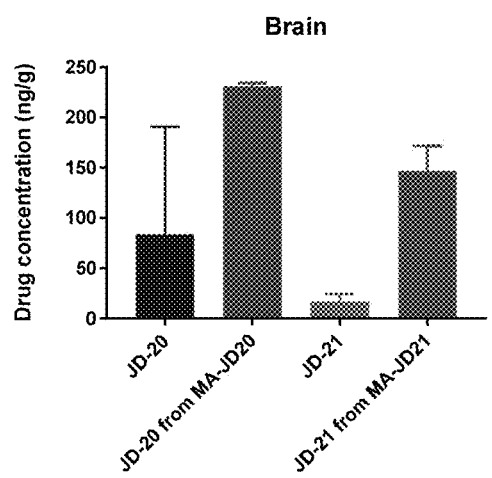
FIG. 5A is a plot of drug concentration the brain of C57Bl/6 mice following systemic administration.

Both amides MA-JD20 and MA-JD21 delivers more of the parent drugs to the CNS compared to unmodified JD-20 or JD-21 from an equimolar systemic dose of 3.05 µmol/kg, as shown in FIG. 5A.

Figure 5B:
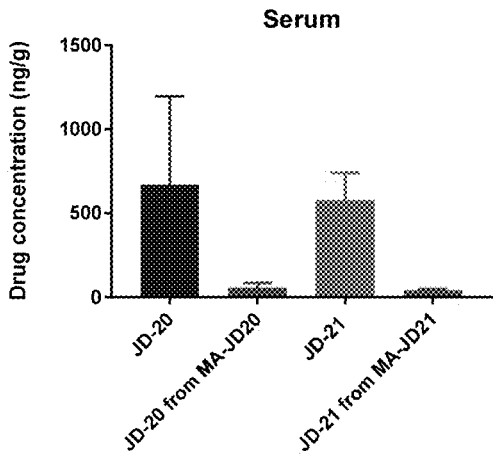
FIG. 5B is a plot of drug concentration in the serum of C57Bl/6 mice following systemic administration.
Figure 5C:
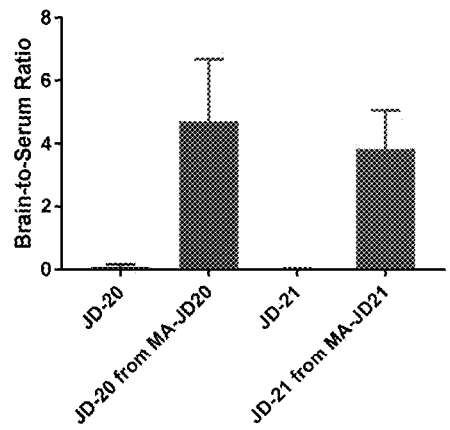
FIG. 5C shows the ratio brain concentration to serum concentration of drugs in C57Bl/6 mice following systemic administration.
Figure 6A:
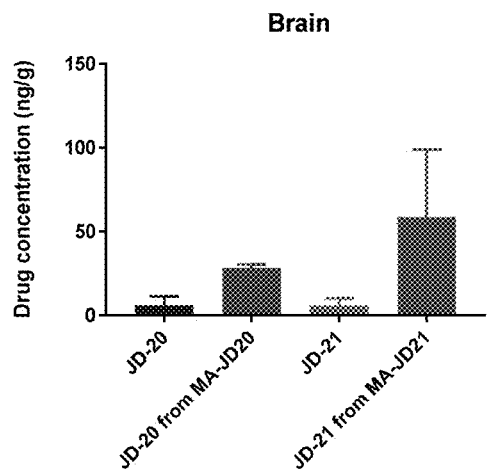
FIG. 6A is a plot of drug concentration in the brain of C57Bl/6 mice following oral administration.
Figure 6B:
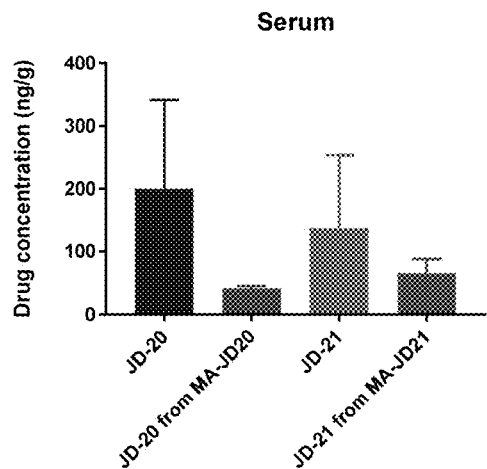
FIG. 6B is a plot of drug concentration in serum if C57Bl/6 mice following oral administration.
Figure 6C:
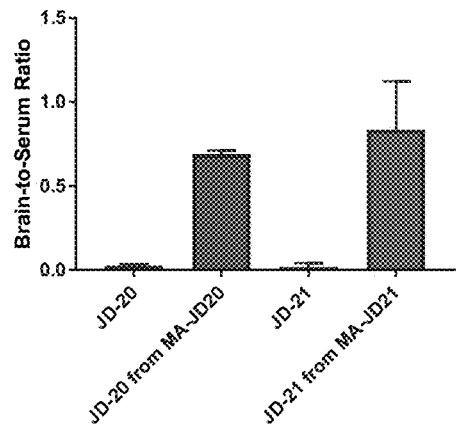
FIG. 6C shows the ratio brain concentration to serum concentration of drugs in C57Bl/6 mice following oral administration.

It was also observed that both amides reduce the peripheral exposure of the corresponding parent drug as shown in FIG. 5B. This decreased serum concentration also supports the fact that these amides considerably improved the CNS distribution of the corresponding parent drug. By comparing the brain to serum ratios of the amides with the unmodified compounds, it was observed that the amides reduced peripheral exposure of the parent drugs in serum by more than four fold (FIG. 5C). Similar results were observed with oral administration using the same dose, i.e. 3.05 µmol/kg (FIG. 6)

Figure 7A:
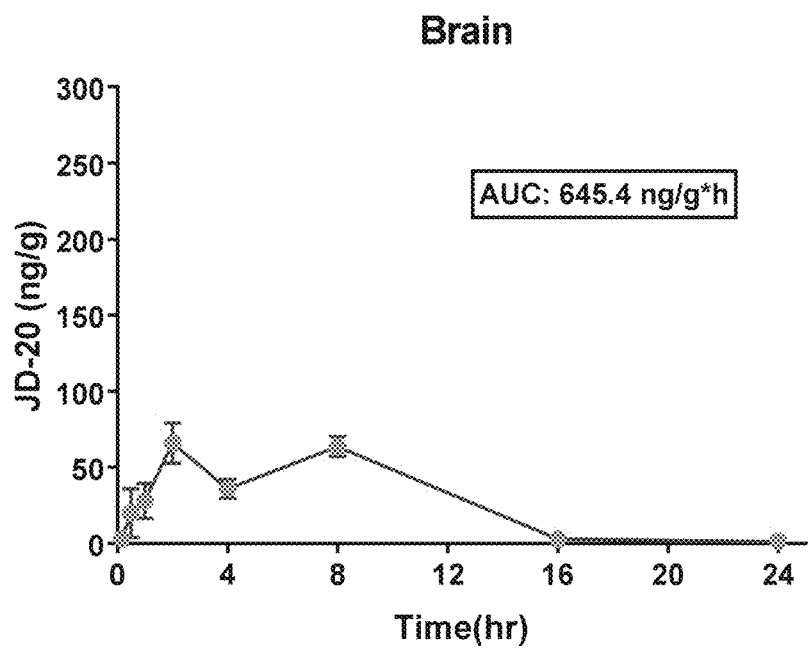
FIG. 7A shows a plot of JD-20 concentration in the brain over a 24 h time-course study following oral administration of the compound to mice.
Figure 7B:
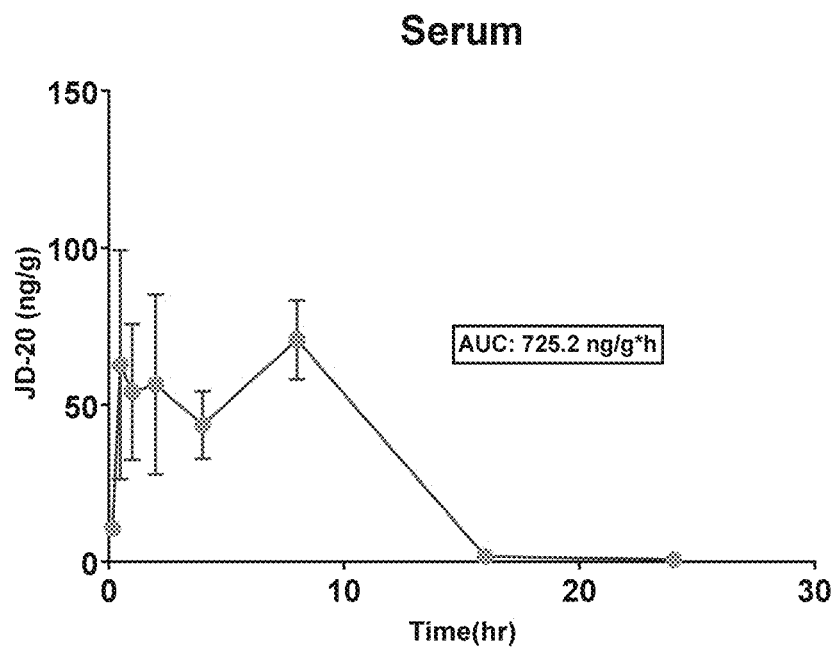
FIG. 7B shows a plot of JD-20 concentrations in the serum over a 24 h time-course study following oral administration of the compound to mice.

Following the single time point drug distribution evaluation, to further understand the pharmacokinetic properties of the amide, a 24 h time-course study was conducted by administering an oral dose of 9.14 µmol/kg of MA-JD20 to mice. The JD-20 concentrations generated in brain and blood were analyzed and area under the curve (AUC) values for brain and serum were obtained (FIG. 7). The $AUC_{brain}/AUC_{serum}$ ratio for amide MA-JD-20 is observed to be 0.89. The $C_{max}$ and $T_{max}$ seemed to be around 2 h in the brain tissue whereas in the blood the $C_{max}$ and $T_{max}$ occurred between the initial 30 to 45 min time points. This fact suggests that the hydrolysis rate of the amide is slow once it reaches the CNS. The results obtained from the single point drug distribution were confirmed by the AUC analyses.

Figure 8:
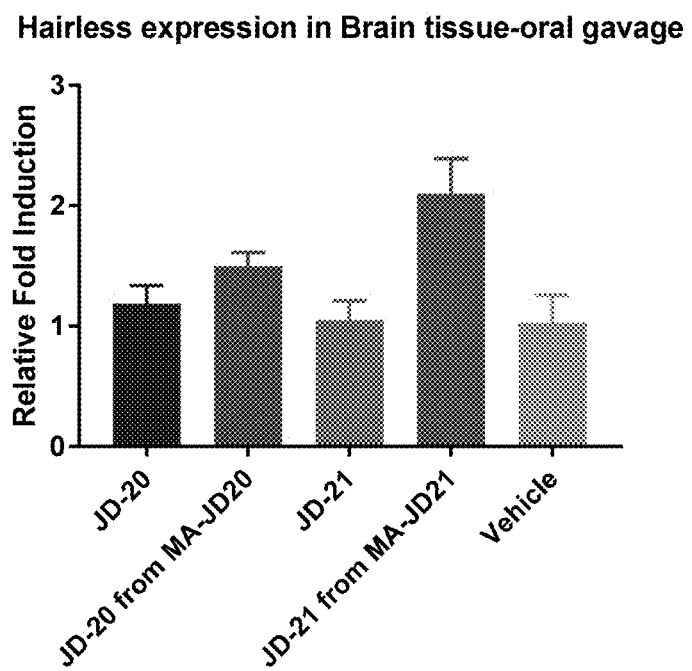
FIG. 8 shows the induction of Hr gene expression by JD-20, MA-JD20, JD-21, and MA-JD21 following oral administration of the compounds to mice.

Having shown that the amides MA-JD20 and MA-JD21 deliver more of the parent drugs to the CNS, both by systemic and oral administration, we evaluated next if the amides upregulate the thyroid responsive Hairless (Hr) gene to a greater extent than the corresponding unmodified compounds. Mice were orally administered a dose of 3.05 µmol/kg (three mice per dose) of JD-20, JD-21, MA-JD20 and MA-JD21 and vehicle (1:1 saline/DMSO). The brain tissues collected were processed according to a protocol for RNA extraction using Trizol reagent and the PureLink RNA mini kit; cDNA was made using the Qiagen QuantiTect Reverse Transcription kit and expression of the Hairless (Hr) gene was measured by qPCR using the QuantiTect SYBR green PCR kit from Qiagen as described earlier. Glyceraldehyde-3-phosphate dehydrogenase (GAPDH) was the housekeeping gene used for normalizing between samples. Data analysis was done by using the comparative CT method to monitor the relative differences in Hr gene expression. The result is shown in FIG. 8. This data is in agreement with the results obtained from the drug distribution studies.

Example 18. Halogenated Amides are Substrates for Fatty-Acid Amide Hydrolase (FAAH)

Materials. Sobetirome and $d_6$-sobetirome were synthesized as previously described. (Placzek and Scanlan. *Tetrahedron* 2015, 71 (35), 5946-5951). Anandamide was purchased from Cayman (90050). Arachidonic acid was purchased from Signma (23401). dii-arachidonic acid was purchased from Avanti (861810E). Solvents were HPLC grade from Fisher. Human FAAH cDNA in a pcDNA4 backbone was kindly provided by Prof. Martin Kaczocha (Stony Brook). A C-terminal FLAG sequence was inserted by PCR using the following primers: 5'-CGCAAATGGGCGGTAGGCGTG (CMV forward) and 5'-AGACTCGAGTCACTTGTCGT-CATCGTCTTTGTAGTCGGATGACTGCTTTTCAGGG GTCAT. The Kpn1/Xho1 digestion fragment was reinserted back into pcDNA4. The resulting pcDNA4-FAAH-FLAG construct was confirmed by sequencing.

LC/MS-MS.

Compound quantification was performed by LC-MS/MS as previously described with modifications (Ferrara, and Scanlan, et al. *Biorg. Med. Chem.* 2017, 25(10) 2743-2753). Chromatography was performed on a Hamiliton PRP-C18 column (5 µm, 2.1×50 mm, 100 Å) fit with a Betabasic precolumn (Thermo). The gradient mobile phase was delivered at a flow rate of 0.5 mL/min, and consisted of two solvents, A: 10 mM ammonium formate in water and B: 10 mM ammonium formate in 90% acetonitrile, 10% water. The gradient was as follows: 0-0.5 min, hold 10% B; 0.5-5.1 min, 10-98% B; 5.1-7 min, hold 98% B; 7-7.1 min, 98-10% B; 7.1-8 min, hold 10%. Analytes were identified in negative mode with multiple-reaction-monitoring (MRM) primarily using parent ion m/z and the strongest resulting second transition with energies optimized for the transitions.

FAAH Activity in Cell Homogenate.

COS-7 cells (ATCC CRL-1651) were cultured in Dulbecco's Modified Eagle's Medium supplemented with 10% FBS, penicillin (100 units/L), and streptomycin (100 µg/L). Cells (800,000/well) were seeded into 6-well plates (Falcon 353046) and left to adhere overnight. Cells were transfected with pcDNA4-FAAH-FLAG with Lipofectamine 2000 (Invitrogen) according to the manufacturer's protocol. Mock transfection controls were done with transfection reagent and no DNA. Cells were washed 4-days post transfection with cold PBS and scraped into TE buffer (125 mM Tris, 1 mM EDTA, pH 9) and sonicated (10 sec, 60 Sonic Dismembrator, Fisher). Cell homogenates were stored at −80° C. and protein concentrations were determined by BCA (Pierce).

Cell homogenates were diluted into TE buffer containing 0.1% fatty-acid free BSA (Alfa Aesar). Substrates were added as 50× stocks in DMSO into 504 aliquots of homogenate to a final concentration of 100 µM. Reactions were performed with homogenate protein at 31.25 µg/mL for 15 min at 37° C. Reactions were quenched with 1004 acetonitrile and vortexed for 20 s. Samples were clarified by centrifuge (10,000 rpm, 15 min, 4° C.). The supernatant is diluted 50-fold into 2:1 MeCN:H2O containing 300 nM dii-arachindonic acid and 30 nM $d_6$-sobetirome. Samples were centrifuged again (13,200 rpm, 15 min, 4° C.). Products were quantified by LC/MS-MS with standard curves generated from mock samples. Observed rates are expressed as nmol product per mg protein homogenate per min.

Figure 9:
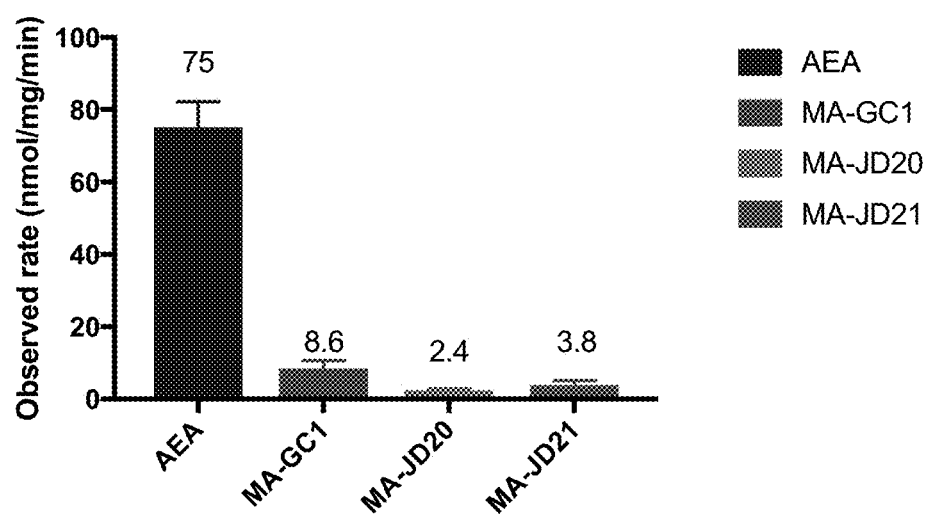
FIG. 9 shows that MA-JD20 and MA-JD21 are substrates for fatty-acid amide hydrolase (FAAH).

FIG. 9 shows that amide MA-JD20 and MA-JD21 are substrates for fatty-acid amide hydrolase (FAAH). FAAH was overexpressed in COS-7 cells as described above and cell homogenate was used to measure observed rates of substrate cleavage compared with the classic endogenous FAAH substrate anandamide (AEA). Substrate were all tested at 100 µM. Compared to AEA, the thyromimetic amides MA-GC1 (9-fold), MA-JD20 (31-fold), and MA-JD21 (20-fold) show decreased rates. However, the these decreased observed rates are comparable to other known endogenous substrates of FAAH (Boger, et al. *Bioorg. Med. Chem. Lett.* 2000, 10 (23), 2613-2616; Cravat, et al. *Proc. Natl. Acad. Sci. U S. A.* 2001, 98 (16), 9371-6) and the halogenated derivatives are close to the activity of the sobetirome amide. Observed rates are expressed as nmol product per mg homogenate protein per min.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A method of treating a neurodegenerative disorder, the method comprising administering an effective amount of a compound of Formula (I):

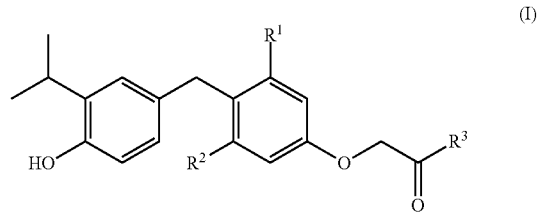

or a pharmaceutically acceptable salt thereof, to a subject in need thereof, thereby treating the neurodegenerative disorder, wherein $R^1$ and $R^2$ are both chloro, $R^3$ is —$NHR^{3b}$ and $R^{3b}$ is methyl.

2. The method of claim 1, wherein the neurodegenerative disorder is a demyelinating disease.

3. The method of claim 1, where the neurodegenerative disorder is X-linked adrenoleukodystrophy.

4. A unit dosage form comprising a compound of Formula (I):

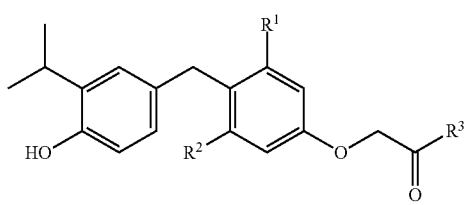

wherein:
R¹ and R² are independently fluoro, chloro, bromo, or iodo;
R³ is —OH or —NR³ᵃR³ᵇ;
R³ᵃ is hydrogen or $C_{1-6}$ alkyl; and
R³ᵇ is $C_{1-6}$ alkyl;
or a pharmaceutically acceptable salt thereof.

5. The unit dosage form of claim 4, wherein R¹ and R² are independently chloro or bromo, or a pharmaceutically acceptable salt thereof.

6. The unit dosage form of claim 4, wherein R¹ and R² are both bromo, or a pharmaceutically acceptable salt thereof.

7. The unit dosage form of claim 6, wherein R³ is OH, and the compound has the following structure:

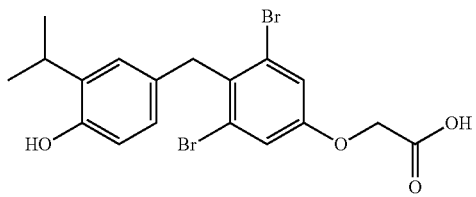 [SMILES: CC(C)c1cc(Cc2c(Br)cc(OCC(=O)O)cc2Br)ccc1O]

a pharmaceutically acceptable salt thereof.

8. The unit dosage form of claim 7, wherein the compound is in the form of the free acid.

9. The unit dosage form of claim 8, wherein the unit dosage form is a tablet or capsule.

10. The unit dosage form of claim 6, wherein R³ is —NHR³ᵇ and R³ᵇ is $C_{1-6}$ alkyl, or a pharmaceutically acceptable salt thereof.

11. The unit dosage form of claim 10, wherein R³ᵇ is methyl, and the compound has the following structure:

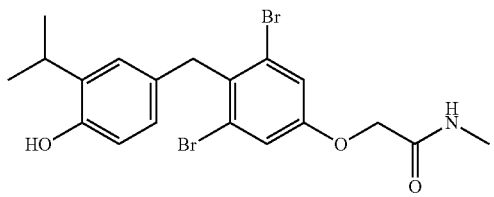 [SMILES: CNC(=O)COc1cc(Br)c(Cc2ccc(O)c(C(C)C)c2)c(Br)c1]

or a pharmaceutically acceptable salt thereof.

12. The unit dosage form of claim 11, wherein the compound is in the form of the free base.

13. The unit dosage form of claim 12, wherein the unit dosage form is a tablet or capsule.

14. The unit dosage form of claim 4, wherein R¹ and R² are both chloro, or a pharmaceutically acceptable salt thereof.

15. The unit dosage form of claim 14, wherein R³ is —OH, and the compound has the following structure:

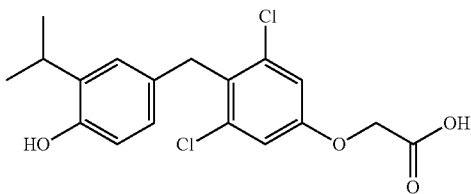

a pharmaceutically acceptable salt thereof.

16. The unit dosage form of claim 15, wherein the compound is in the form of the free acid.

17. The unit dosage form of claim 16, wherein the unit dosage form is a tablet or capsule.

18. The unit dosage form of claim 14, wherein R³ is —NHR³ᵇ and R³ᵇ is $C_{1-6}$ alkyl, or a pharmaceutically acceptable salt thereof.

19. The unit dosage form of claim 18, wherein R³ᵇ is methyl, and the compound has the following structure:

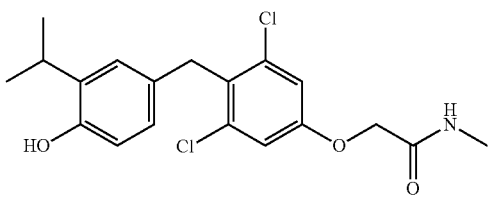

or a pharmaceutically acceptable salt thereof.

20. The unit dosage form of claim 19, wherein the compound is in the form of the free base.

21. The unit dosage form of claim 20, wherein the unit dosage form is a tablet or capsule.

22. A method of treating a neurodegenerative disorder, the method comprising administering to a subject in need thereof an effective amount of a unit dosage form of claim 4.

23. The method of claim 22, wherein the neurodegenerative disorder is a demyelinating disease.

24. The method of claim 22, wherein the neurodegenerative disorder is X-linked adrenoleukodystrophy.

25. The method of claim 22, wherein the neurodegenerative disorder is multiple sclerosis.

* * * * *